(12) United States Patent
Killer et al.

(10) Patent No.: US 11,355,303 B2
(45) Date of Patent: Jun. 7, 2022

(54) SYSTEMS, DEVICES, AND METHODS FOR CONTAMINANT RESISTANT INSULATIVE STRUCTURES

(71) Applicant: TAE TECHNOLOGIES, INC., Foothill Ranch, CA (US)

(72) Inventors: Christopher J. Killer, Costa Mesa, CA (US); Vladislav Vekselman, Lake Forest, CA (US); Joshua Leuenberger, Mission Viejo, CA (US)

(73) Assignee: TAE TECHNOLOGIES, INC., Foothill Ranch, CA (US)

(*) Notice: Subject to any disclaimer, the term of this patent is extended or adjusted under 35 U.S.C. 154(b) by 0 days.

(21) Appl. No.: 17/006,049

(22) Filed: Aug. 28, 2020

(65) Prior Publication Data

US 2021/0151308 A1    May 20, 2021

Related U.S. Application Data

(60) Provisional application No. 63/044,313, filed on Jun. 25, 2020, provisional application No. 62/895,203, filed on Sep. 3, 2019.

(51) Int. Cl.
*H01J 37/12* (2006.01)
*A61N 5/10* (2006.01)
*H01J 49/06* (2006.01)
*H01J 27/02* (2006.01)

(52) U.S. Cl.
CPC ............ *H01J 37/12* (2013.01); *A61N 5/1077* (2013.01); *A61N 2005/109* (2013.01); *H01J 27/024* (2013.01); *H01J 49/068* (2013.01); *H01J 2237/038* (2013.01)

(58) Field of Classification Search
CPC ................... H01J 49/068; H01J 2237/038
See application file for complete search history.

(56) References Cited

U.S. PATENT DOCUMENTS

| 4,900,982 | A | 2/1990 | Kolpin |
| 5,521,389 | A | 5/1996 | Kim |
| 2010/0072402 | A1 | 3/2010 | Satoh et al. |
| 2013/0206999 | A1 | 8/2013 | Shimazu |
| 2014/0183354 | A1* | 7/2014 | Moon .................. H01J 49/164 250/287 |
| 2014/0210337 | A1* | 7/2014 | Setsuhara ............. C23C 14/358 313/356 |
| 2017/0103879 | A1 | 4/2017 | Cooks et al. |
| 2019/0295832 | A1* | 9/2019 | Waki .................... H01J 49/421 |

OTHER PUBLICATIONS

International Search Report and Written Opinion for PCT/US2020/048459, ISA/US, dated Nov. 17, 2020, (13 pages).

* cited by examiner

*Primary Examiner* — Eliza W Osenbaugh-Stewart
(74) *Attorney, Agent, or Firm* — Alston & Bird LLP

(57) ABSTRACT

Embodiments of systems, devices, and methods relate to an electrode standoff isolator. An example electrode standoff isolator includes a plurality of adjacent insulative segments positioned between a proximal end and a distal end of the electrode standoff isolator. A geometry of the adjacent insulative is configured to guard a surface area of the electrode standoff isolator against deposition of a conductive layer of gaseous phase materials from a filament of an ion source.

19 Claims, 15 Drawing Sheets

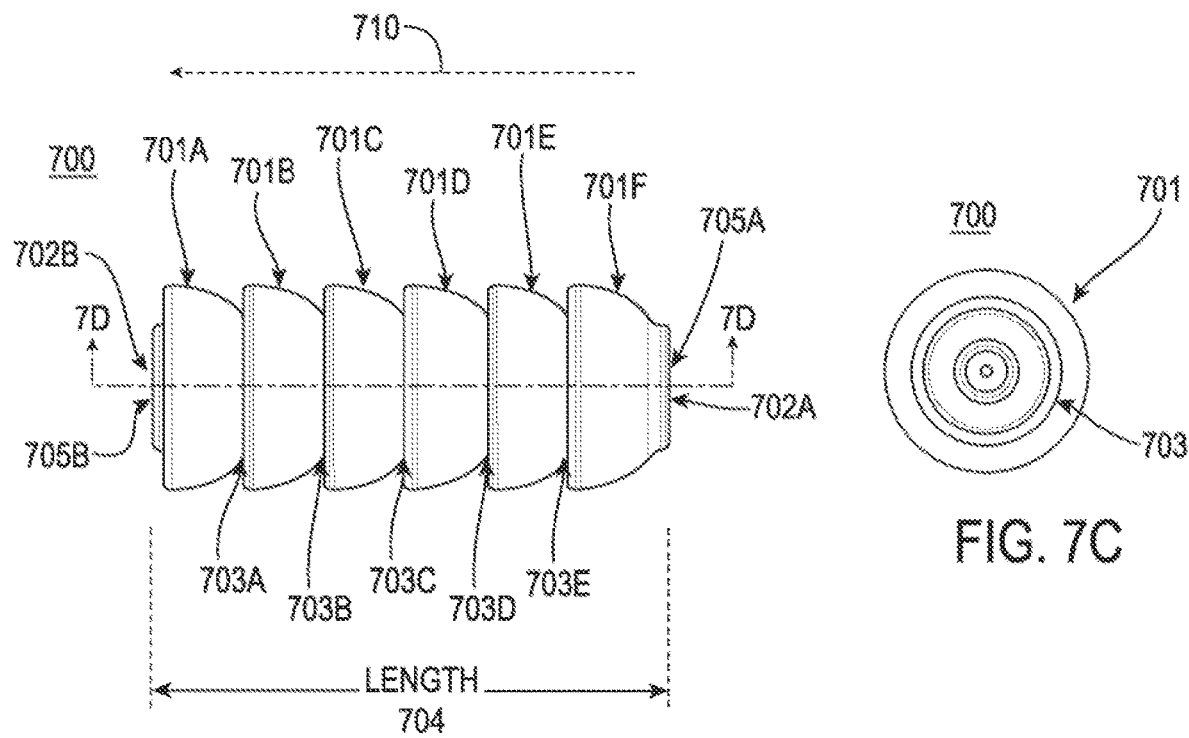
FIG. 7B
FIG. 7C
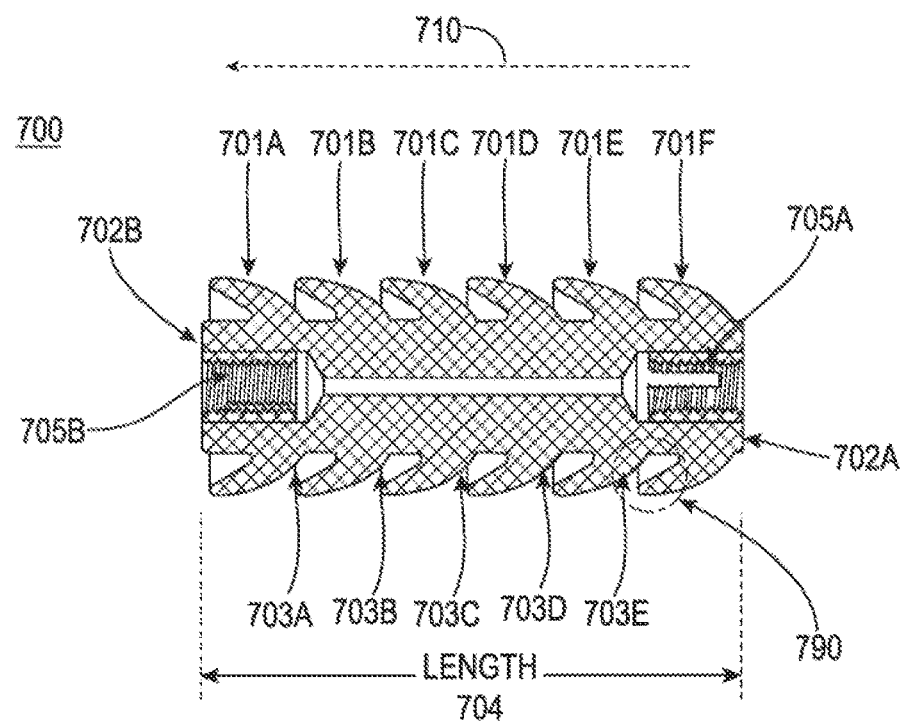
FIG. 7D

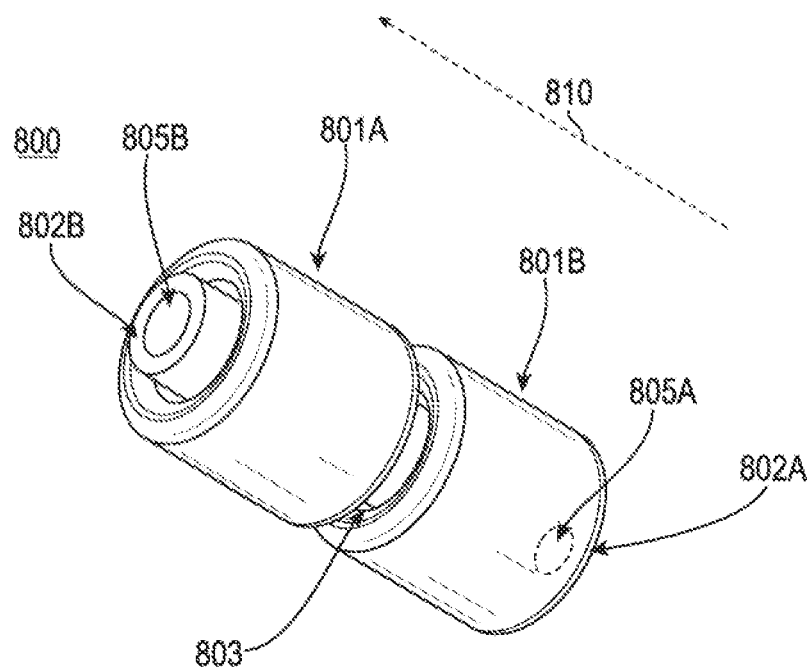
FIG. 8A
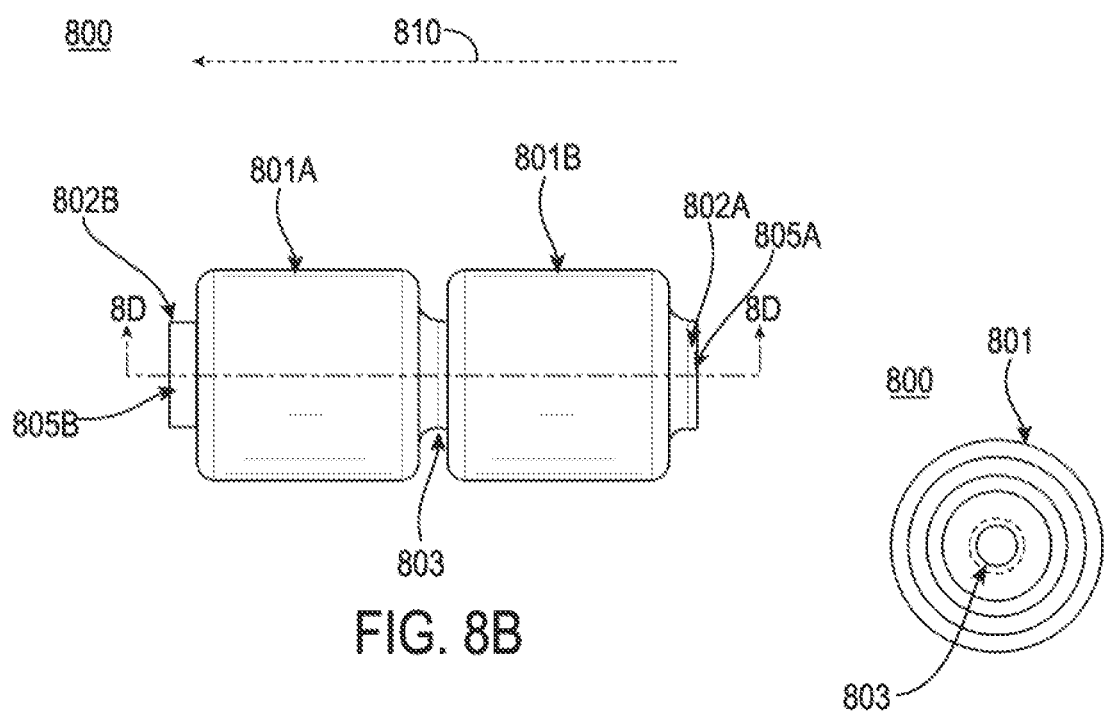
FIG. 8B
FIG. 8C

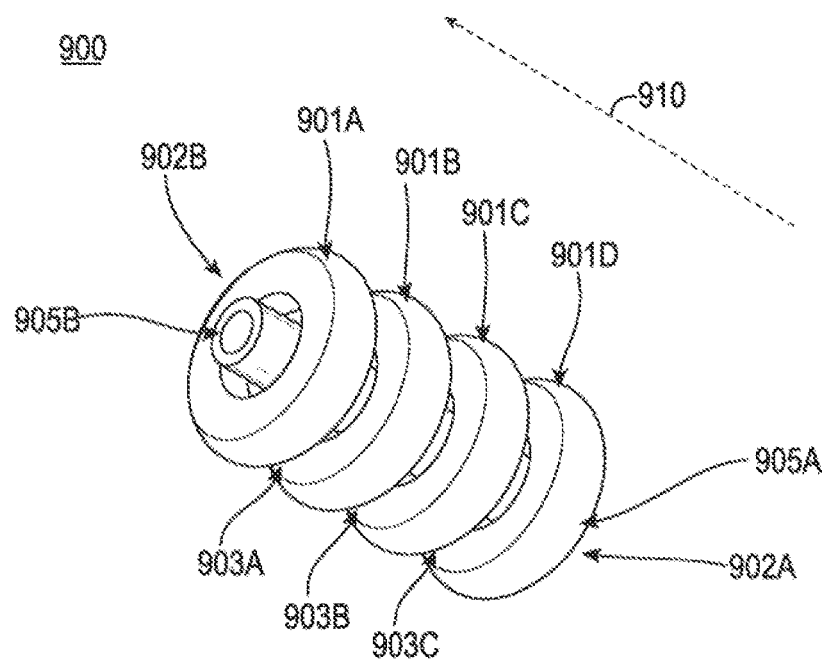
FIG. 9A
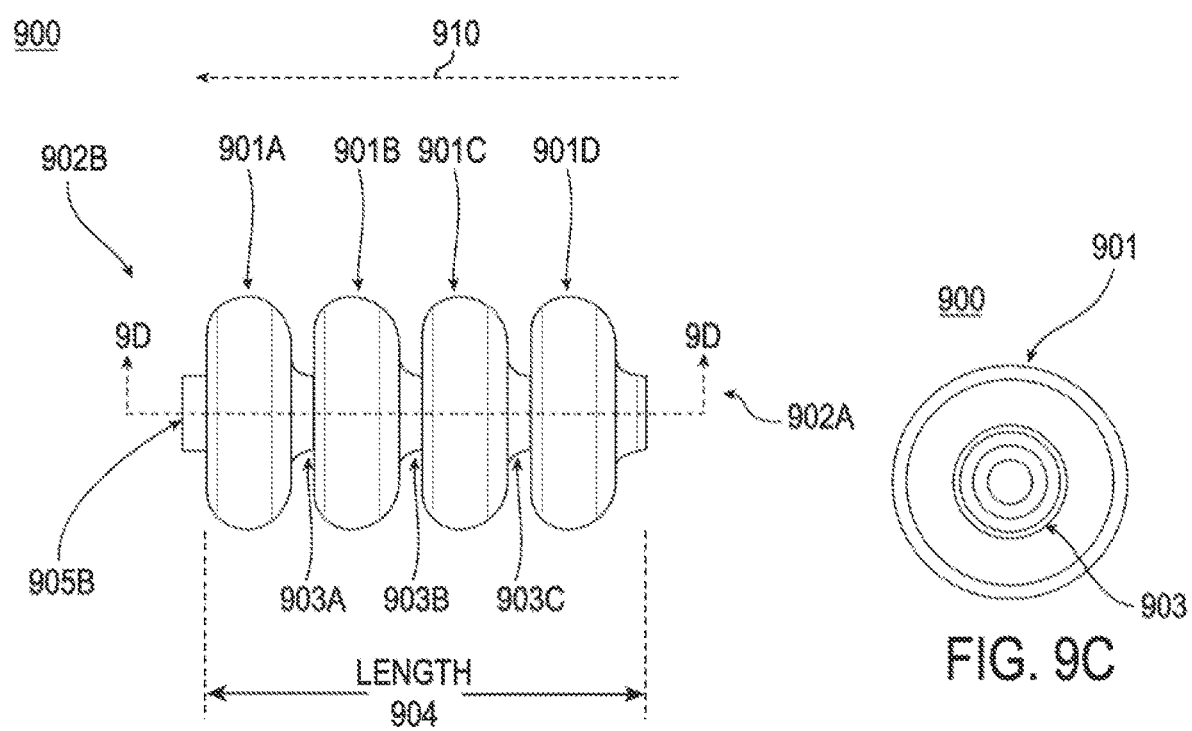
FIG. 9B
FIG. 9C

SYSTEMS, DEVICES, AND METHODS FOR CONTAMINANT RESISTANT INSULATIVE STRUCTURES

CROSS-REFERENCE TO RELATED APPLICATIONS

The present application claims priority to U.S. Provisional Application Ser. No. 63/044,313, titled "SYSTEMS, DEVICES, AND METHODS FOR CONTAMINANT RESISTANT INSULATIVE STRUCTURES," filed Jun. 25, 2020, and to U.S. Provisional Application Ser. No. 62/895,203, titled "EINZEL LENS FOR LOW ENERGY ION BEAM TRANSPORT," filed Sep. 3, 2019, all of which are incorporated herein by reference in their entirety.

FIELD

The subject matter described herein relates generally to systems, devices with contaminant resistant insulative structures and their methods of use and manufacture.

BACKGROUND

Extraction of ions and formation of an ion beam is one of the most critical points in beam technology. In ion beam systems utilizing plasma-based ion sources, ions can be extracted from a boundary surface (called a meniscus) of the plasma. The shape and parameters of the plasma boundary surface are characterized by strong dependence on the extracted current density, local rates of ionization, recombination and diffusion, and applied electric field distribution. Even Pierce's law, promoting formation of a perfectly parallel electron beam, fails for extraction of ions. Therefore, a newborn ion beam is typically highly divergent, aberrant (effect of the magnetic dipole separating electrons and ions of the same polarity) and subjected to space charge effects due to low initial energy (e.g., about 30 kiloelectron volts (keV)). As a result, a focusing ion-optics component is needed proximate to the ion beam formation region to initiate beam transport.

Certain criteria of the initial ion-optics component tend to be dictated by ion source design and operation. For example, in a neutron beam system for cancer radiation therapy, the design and operation of the ion source requires the ion-optics component to be compact (to allow placement closest the beam formation region), feature high focusing power, withstand beam thermal load, and provide reliable and stable operation in dc and pulsed mode of the ion beam generation in a wide range of extracted currents (e.g., 1-20 milliamps (mA)).

Although there are several conventional types of ion-optics components able to satisfy some of the criteria listed above, there is none capable of satisfying all of the listed criteria. Therefore, fine tuning of the selected ion-optics component becomes extremely important to fulfill all the requirements dictated by a particular application.

The temperature of the filaments within an ion source is sufficient for evaporation of the filament material, which in turn leads to diffusion of the gaseous phase filament material into the region of any ion optics components located immediately downstream of the source, and beyond. Further, the gaseous phase filament material can be partially ionized due to interactions with ion beam particulates. The flux of neutral and ionized particles (e.g., evaporated from the filament) towards electrically insulative (non-conductive) surfaces within the ion optics components (e.g., standoff isolation) forms an electrically conductive layer on the mount surface. The contaminant electrically conductive layer on the surface of the insulative structure can defeat the structure's insulative protection by the occurrence of electrical losses, shorting, or arcing, which leads to required system maintenance or insulator replacement.

For these and other reasons, a need exists for improved, efficient, and compact systems, devices, and methods that enable contaminant resistant insulative structures.

SUMMARY

Embodiments of systems, devices, and methods relate to contaminant resistant insulative structures. An example of such is an electrode standoff isolator, where the contaminant resistant structure includes a plurality of adjacent insulative segments positioned between a proximal end and a distal end of the electrode standoff isolator. A geometry of the adjacent insulative segments provides surface area of the electrode standoff isolator that is less subjected to deposition of a conductive layer of gaseous phase materials from a filament of an ion source.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 7A, 7B, 7C, and 7D illustrate an example embodiment of an electrode standoff isolator, for use with embodiments of the present disclosure.

FIGS. 8A, 8B, 8C, and 8D illustrate an example embodiment of an electrode standoff isolator, for use with embodiments of the present disclosure.

FIGS. 9A, 9B, 9C, and 9D illustrate an example embodiment of an electrode standoff isolator, for use with embodiments of the present disclosure.

DETAILED DESCRIPTION

Figure 1A:
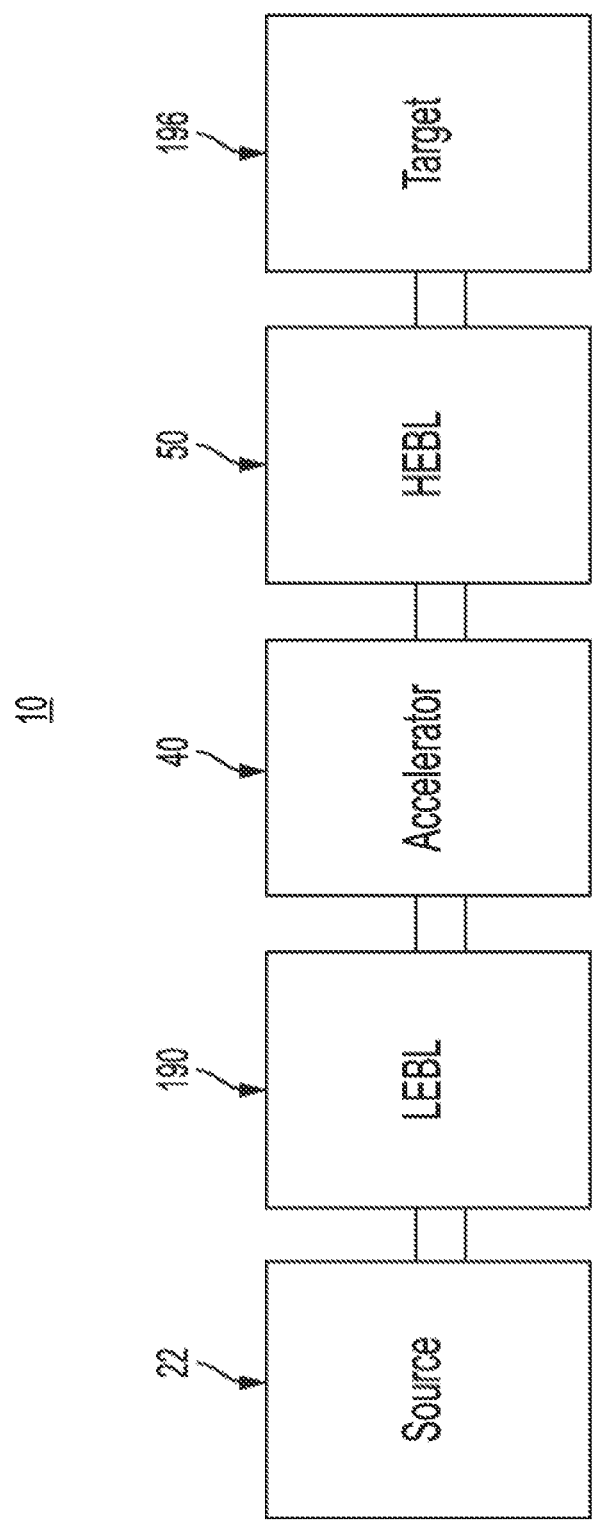
FIG. 1A is a schematic diagram of an example embodiment of a neutron beam system for use with embodiments of the present disclosure.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutral, as well as a species having more than one electron, proton, and/or neutron (e.g., other ions, atoms, and molecules).

Example embodiments of systems, devices, and methods are described herein for electrode standoff isolators for use in an einzel lens used in conjunction with a neutron beam system (e.g., including a particle accelerator). The embodiments described herein can be used with any type of particle accelerator or in any particle accelerator application involving production of a charged particle beam at specified energies for supply to the particle accelerator.

Embodiments of the present neutron beam system can be used in numerous applications, an example of which is as a neutron beam system for generation of a neutron beam for use in boron neutron capture therapy (BNCT). For ease of description, many embodiments described herein will be done so in the context of a neutron beam system for use in BNCT, although the embodiments are not limited to just neutron beams nor BNCT applications.

Solutions for the generation and transport of negative hydrogen ion beams include magnetic focusing devices (e.g., a solenoid), electrostatic and magnetic quadrupoles, and einzel lenses. Magnetic solenoids are used on negative ion sources including both plasma volumetric and cesium-doped plasma surface ion sources. The main advantage of magnetic ion optics components is the absence of high electric fields. The latter excludes all the processes related to the formation of electrical discharges and breakdowns between beam line components. However, the focusing power of the magnetic field utilized in solenoids is proportional to the ion's energy. Thus, for low energy ion beam, strong magnetic fields (and gradients) are required. The latter brings up issues related to the penetration of the magnetic field into the adjacent beam line components and into the ion's extraction region. The presence of the magnetic field is likely to complicate the characterization of the ion source and ion beam. Strong magnetic fields also require high currents in the solenoid winding, which creates an additional heat source. These considerations limit the distance from where the solenoid can be installed.

Quadrupoles, both electrostatic and magnetic, are bulky and complex. With most of considerations discussed above with regard to solenoids being applicable to quadrupoles, application of both solenoids and quadrupoles are found in high energy beam lines. Both magnetic focusing devices and quadrupole devices can be used in regions of beam systems susceptible to deposition of an electrically conductive material on insulative structures of those devices.

As discussed above, the einzel lens, which is routinely used for the transportation of electron and positive ion beams, is an electrostatic device focusing and guiding the transportation of low energy ion beams. However, the physics of processes related to the interaction of negative ions with solid components of the beam line and in free space, e.g., surface/volume recombination, charge-exchange, induced secondary electron/ion emission, etc., is an area of research.

When an electrostatic device such as an einzel lens is used with a high voltage ion source for an ion beam system, an electrode within the einzel lens is preferably mounted using materials that can provide electrical insulation sufficient to stand off potential between surfaces. While the standoff isolators preferably provide electrical insulation sufficient to stand off any potential difference between the surfaces of the mount plate and the powered electrode of an einzel lens, the standoff isolators provide a surface upon which contaminants may form a conductive layer, leading to elimination of the insulation provided by the standoff isolators and defeating their purpose.

For example, a biased electrode within an einzel lens, as in various high voltage applications such as an ion source, is preferably mounted using materials that can provide electrical insulation sufficient to stand off potential between surfaces.

While the standoff isolators preferably provide electrical insulation sufficient to stand off any potential difference between the surfaces of the mount plate and the powered electrode of an einzel lens, the standoff isolators provide a surface upon which contaminants may form a conductive layer, leading to elimination of the insulation provided by the standoff isolators and defeating their purpose. That is, the temperature of the filaments within an ion source is sufficient for evaporation of the filament material, which in turn leads to diffusion of the gaseous phase filament material into the region of the einzel lens. Further, the gaseous phase filament material can be partially ionized due to interactions with ion beam particulates. The flux of neutral and ionized particles (e.g., evaporated from the filament) towards the surface of the mounts for the electrode forms an electrically conductive layer on the mount (e.g., standoff isolator) surface. The electrically conductive layer on the surface of the electrode mount results in poor insulation or a lack of insulation being provided by the mount, which leads to required system maintenance or insulator replacement.

Moreover, the standoff isolators preferably provide sufficient electrical insulation while avoiding impeding passage of an ion beam through the einzel lens.

Conventional materials for mounts (e.g., standoff isolators) suffer from the aforementioned deposition of a conductive layer on the surface of the mounts after extended use (e.g., from nearby ion source filaments running at high temperatures during ion source operation). Conventional approaches to solving the aforementioned challenges include the use of cylindrical glazed ceramic insulator mounts, or the use of cylindrical plastic insulator mounts having a rippled surface. These conventional approaches suffer from an inability to withstand the deposition of the electrically conductive layer on the insulator mount surface for a period of time for successful use in neutron beam and BNCT applications.

While insulating supports for use in attaching electric power distribution or transmission lines to utility poles or transmission towers have been presented, and the insulating supports are designed to shed water, such insulators are inapplicable in equipment designed for neutron beam transport. For example, insulating supports for use with electric power distribution or transmission lines are designed to support the weight of suspended wires without allowing current to flow through a transmission tower to ground, which involves an entirely different scale as compared to beam transport applications. Moreover, such insulating supports may encounter external deposits of rain-water or other environmental dusts as a result of being located outdoors, and such external deposits differ greatly from those contaminants possibly deposited on an insulator mount surface in the context of neutron beam transport (e.g., rainwater evaporates). Further, the present insulator mounts are for operation in a vacuum environment, and are designed according to aspects of such an environment. The present insulator mounts are also designed to withstand the possibility of multi-directional contamination and may be positioned horizontally as opposed to vertically. Finally, the present insulator mounts or standoff isolators are designed to provide one or more shadow regions such that the shadow region is a shaded surface area protected against deposition.

Embodiments of the present disclosure overcome the aforementioned challenges by providing insulative structures having a novel surface design. These insulative structures can be used in a host of different devices (magnetic focusing devices, quadropoles, electrostatic lenses) and roles within a beam system. For ease of illustration, these embodiments will be described in the context of an electrical standoff isolator for use in high voltage electrode mounts in an einzel lens, however these embodiments are not limited to such.

In ion sources, gaseous phase filament particles can tend to travel in a somewhat straight line originating from the upstream ion source through the einzel lens, and therefore past a proximal end of the standoff isolator and then past the distal end of the standoff isolator. Because of collisions and partial ionization, gaseous phase filament particles may deposit on surfaces facing the ion beam yet may not reach surfaces that are not directly exposed to the ion beam. By introducing herein an overhanging rib and controlling its curvature, standoff isolators of the present disclosure introduce surface areas that are less subjected to deposit formation. Surface areas less subjected to deposit formation enable the standoff isolators to function as insulators for extended periods of time and for several uses.

The novel surface design of the present electrical standoff isolator is more resistant to deposition of a conductive layer than conventional cylindrical designs. Accordingly, embodiments of standoff isolators herein include a beneficial geometry for (a) maximizing surface area of the standoff isolator to provide sufficient insulative properties while (b) allowing passage of an ion beam through the einzel lens as well as (c) avoiding deposition of contaminants on the shadowed surface area.

FIG. 1A is a schematic diagram of an example embodiment of a beam system for use with embodiments of the present disclosure. Here, beam system 10 includes a source 22, a low-energy beamline (LEBL) 190, an accelerator 40 coupled to the low-energy beamline (LEBL) 190, and a high-energy beamline (HEBL) 50 extending from accelerator 40 to a target assembly housing a target 196. LEBL 190 is configured to transport a beam from source 22 to accelerator 40, which is configured to accelerate the beam HEBL 50 transfers the beam from an output of accelerator 40 to a target 196.

Figure 1B:
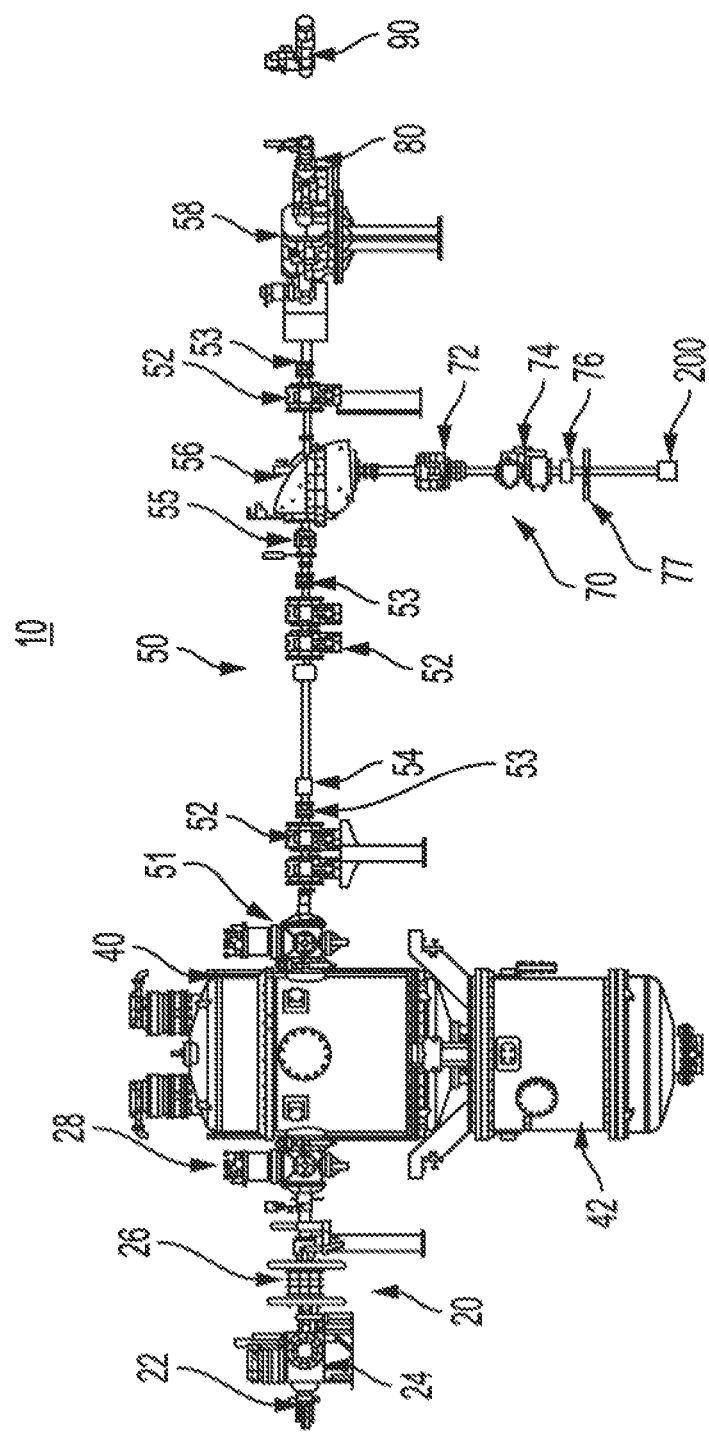
FIG. 1B is a schematic diagram of an example embodiment of a neutron beam system for use in boron neutron capture therapy (BNCT).
Figure 2:
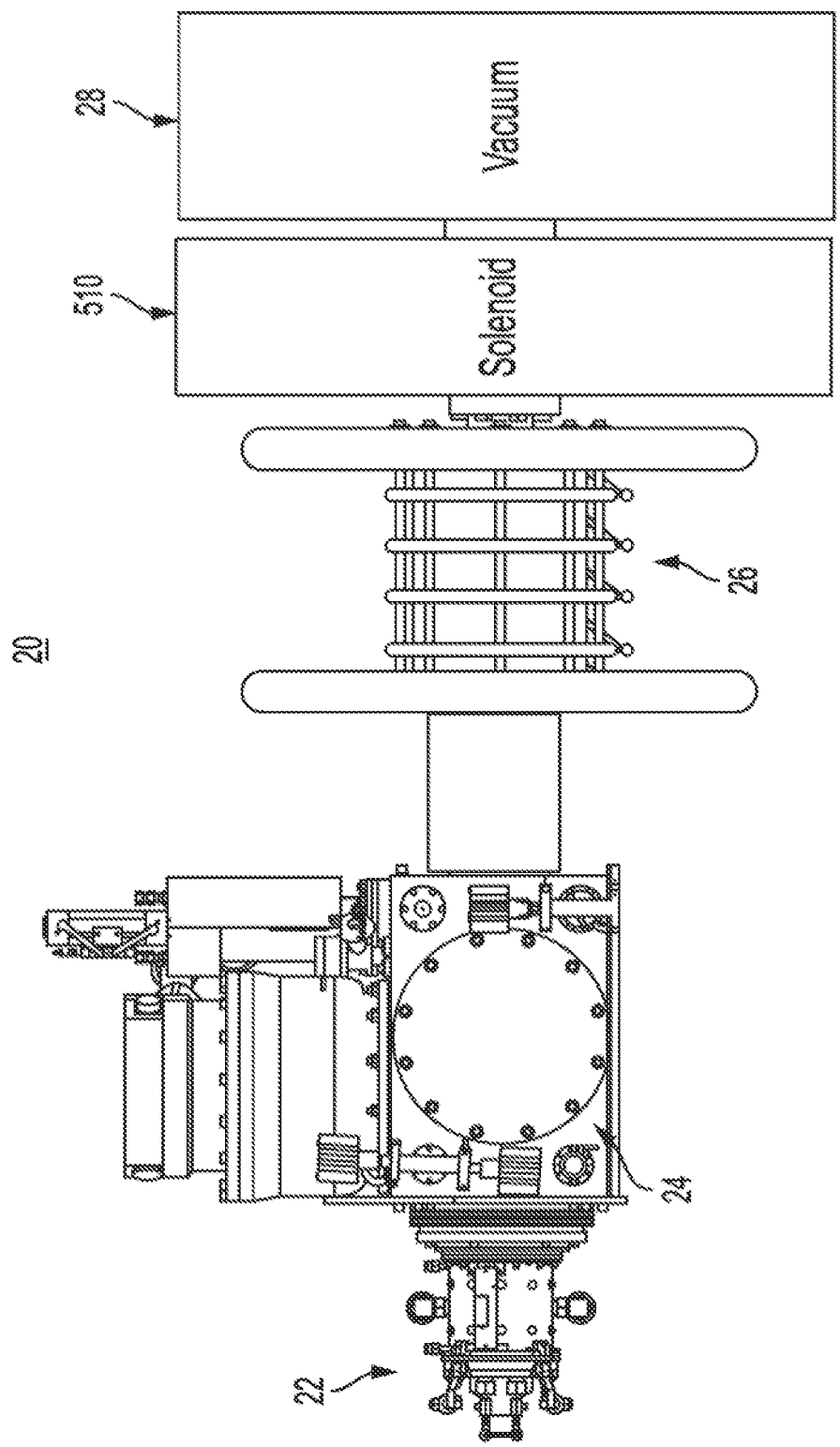
FIG. 2 illustrates an example pre-accelerator system or ion beam injector for use with embodiments of the present disclosure.

FIG. 1B is a schematic diagram illustrating an example neutron beam system 10 for use in boron neutron capture therapy (BNCT), according to embodiments of the present disclosure. The neutron beam system 10 includes a pre-accelerator system 20 forming at least a portion of the LEBL, where the pre-accelerator system 20 serves as a charged particle beam injector as shown in FIG. 2, a high voltage (HV) tandem accelerator 40 coupled to the pre-accelerator system 20, and a high-energy beamline 50 extending from the tandem accelerator 40 to a neutron target assembly 200 housing the neutron-producing target. In this embodiment beam source 22 is an ion source and the charged particle beam is a negative ion beam prior to conversion to a proton beam within tandem accelerator 40. It will be appreciated that neutron beam system 10 as well as pre-accelerator system 20 can also be used for other applications, such as cargo inspection and others, and is not limited to BNCT.

The pre-accelerator system 20 (also referred to herein as the charged particle beam injector or ion beam injector) is configured to transport the ion beam from the ion source 22 to the input (e.g., an input aperture) of the tandem accelerator 40.

Tandem accelerator 40, which is powered by a high voltage power supply 42 coupled thereto, can produce a proton beam with an energy generally equal to twice the voltage applied to the accelerating electrodes positioned within the tandem accelerator 40. The energy level of the proton beam is achieved by accelerating the beam of negative hydrogen ions from the input of the tandem accelerator 40 to the innermost high-potential electrode, stripping two electrons from each ion, and then accelerating the resulting protons downstream by the same applied voltage.

The high-energy beamline 50 transfers the proton beam from the output of the tandem accelerator 40 to the neutron-generating target in the neutron target assembly 200 positioned at the end of a branch 70 of the beamline extending into a patient treatment room. System 10 can be configured to direct the proton beam to any number of one or more targets and associated treatment areas. In this embodiment, the high-energy beamline 50 includes three branches 70, 80 and 90 to extend into three different patient treatment rooms. The high-energy beamline 50 includes a pumping chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, fast beam position monitor 55 section, and a scanning magnet 74.

The design of the high-energy beamline 50 depends on the configuration of the treatment facility (e.g., a single-story configuration of a treatment facility, a two-story configuration of a treatment facility, and the like). The beam can be delivered to a target assembly (e.g., positioned near a treatment room) 200 with the use of the bending magnet 56. Quadrupole magnets 72 can be included to then focus the beam to a certain size at the target. Then, the beam passes one or more scanning magnets 74, which provides lateral movement of the beam onto the target surface in a desired pattern (e.g., spiral, curved, stepped in rows and columns, combinations thereof, and others). The beam lateral movement can help achieve smooth and even time-averaged distribution of the proton beam on the lithium target, preventing overheating and making the neutron generation as uniform as possible within the lithium layer.

After entering the scanning magnets 74, the beam can be delivered into a current monitor 76, which measures beam current. The measured beam current value can be used to operate a safety interlock. The target assembly 200 can be physically separated from the high energy beamline volume with a gate valve 77. The main function of the gate valve is separation of the vacuum volume of the beamline from the target while target exchange/loading. In embodiments, the beam may not be bent by 90 degrees by a bending magnet 56, it rather goes straight to the right, then it enters the quadrupole magnets 52, which are located in the horizontal beamline. After, the beam could be bent by another bending magnet 58 to a needed angle, depending on the room configuration. Otherwise, the bending magnet 58 could be replaced with a Y-shaped magnet in order to split the beamline into two directions for two different treatment rooms located on the same floor.

FIG. 2 illustrates an example of a pre-accelerator system or ion beam injector for use with embodiments of the present disclosure. In this example, pre-accelerator system 20 includes an einzel lens 30 (not visible in FIG. 2, but depicted in FIG. 3), a pre-accelerator tube 26, and a solenoid 510, and is configured to accelerate a negative ion beam injected from ion source 22. The pre-accelerator system 20 is configured to provide acceleration of the beam particles to the energies required for tandem accelerator 40, and to provide overall convergence of the negative ion beam to match input aperture area at an input aperture or entrance of the tandem accelerator 40. In embodiments, the ion source 22 is configured to provide a negative ion beam upstream of the einzel lens 30, and the negative ion beam continues to pass through pre-accelerator tube 26 and a solenoid 510. The solenoid 510 is positioned between the pre-accelerator tube and the tandem accelerator and is electrically couplable with a power supply. The negative ion beam passes through the solenoid 510 to the tandem accelerator 40.

Pre-accelerator system 20 can also include an ion source vacuum box 24, and a pumping chamber 28, which, with pre-accelerator tube 26 as well as other elements are part of a relatively low energy beamline coupled to the tandem accelerator 40. The ion source vacuum box 24, within which the einzel lens 30 is positioned, extends from the ion source 22. The pre-accelerator tube 26 can be coupled to the ion source vacuum box 24, and solenoid 510 can be coupled to the pre-accelerator tube 26. A pumping chamber 28 can be coupled to the solenoid 510 and the tandem accelerator 40. The ion source 22 serves as a source of charged particles which can be accelerated, conditioned and eventually used to produce neutrons when delivered to a neutron producing target. The example embodiments will be described herein with reference to an ion source producing a negative hydrogen ion beam, although embodiments are not limited to such, and other positive or negative particles can be produced by the source. The pre-accelerator system 20 can have zero, one, or multiple magnetic elements for purposes such as focusing and/or adjusting alignment of the beam. For example, any such magnetic elements can be used to match the beam to the beamline axis and the acceptance angle of the tandem accelerator 40. The ion vacuum box 24 may have ion optics positioned therein.

There are two types of negative ion sources 22, which differ by the mechanism of generation of negative ions: the surface type and the volume type. The surface type requires the presence of cesium (Cs) on specific internal surfaces. The volume type relies on formation of negative ions in the volume of a high current discharge plasma. While both types of ion sources can deliver the desired negative ion current for applications related to tandem accelerators, surface type negative ion sources (e.g., with cesium (Cs)) are undesirable for modulation. That is, for modulation of a negative ion beam in embodiments described herein, negative ion sources of the volume type (thus, without employing cesium (Cs)) are preferred.

Figure 3:
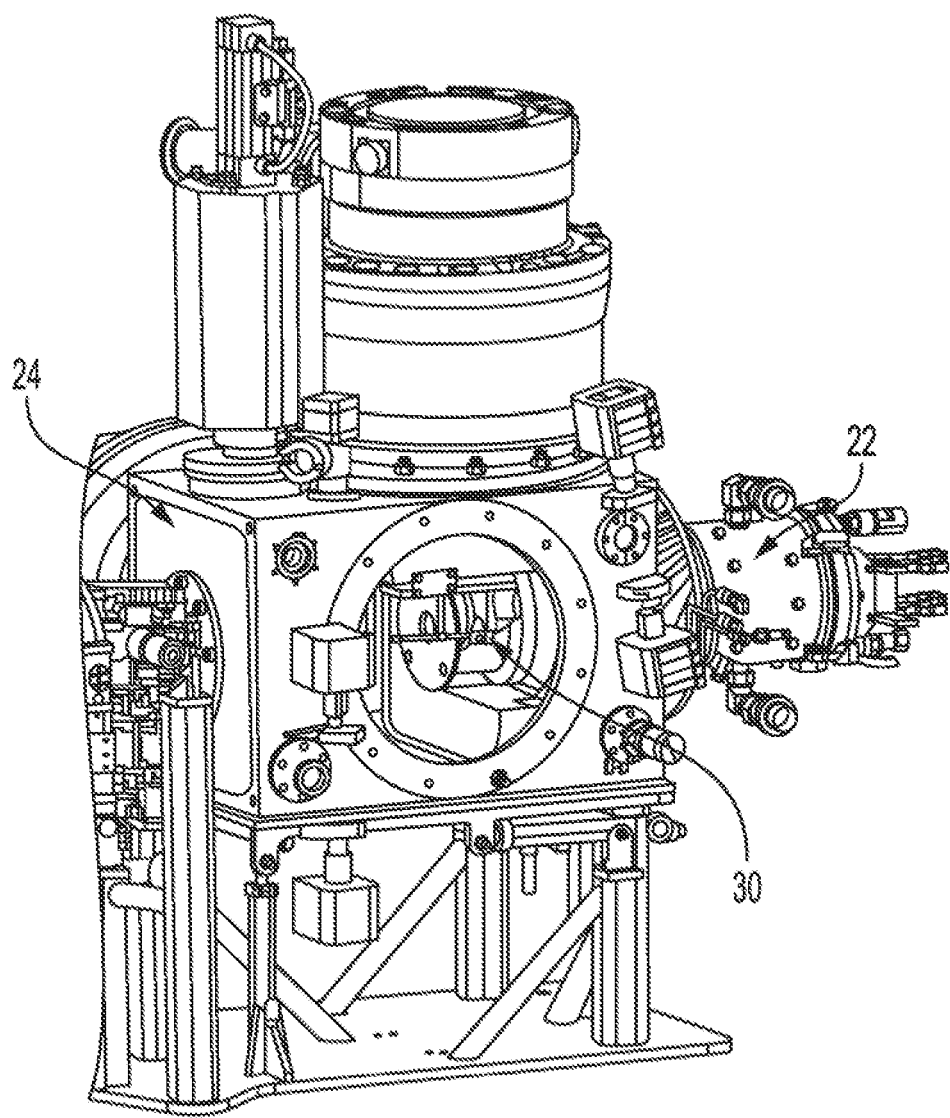
FIG. 3 illustrates the example ion source and ion source vacuum box shown in FIG. 2.
Figure 4:
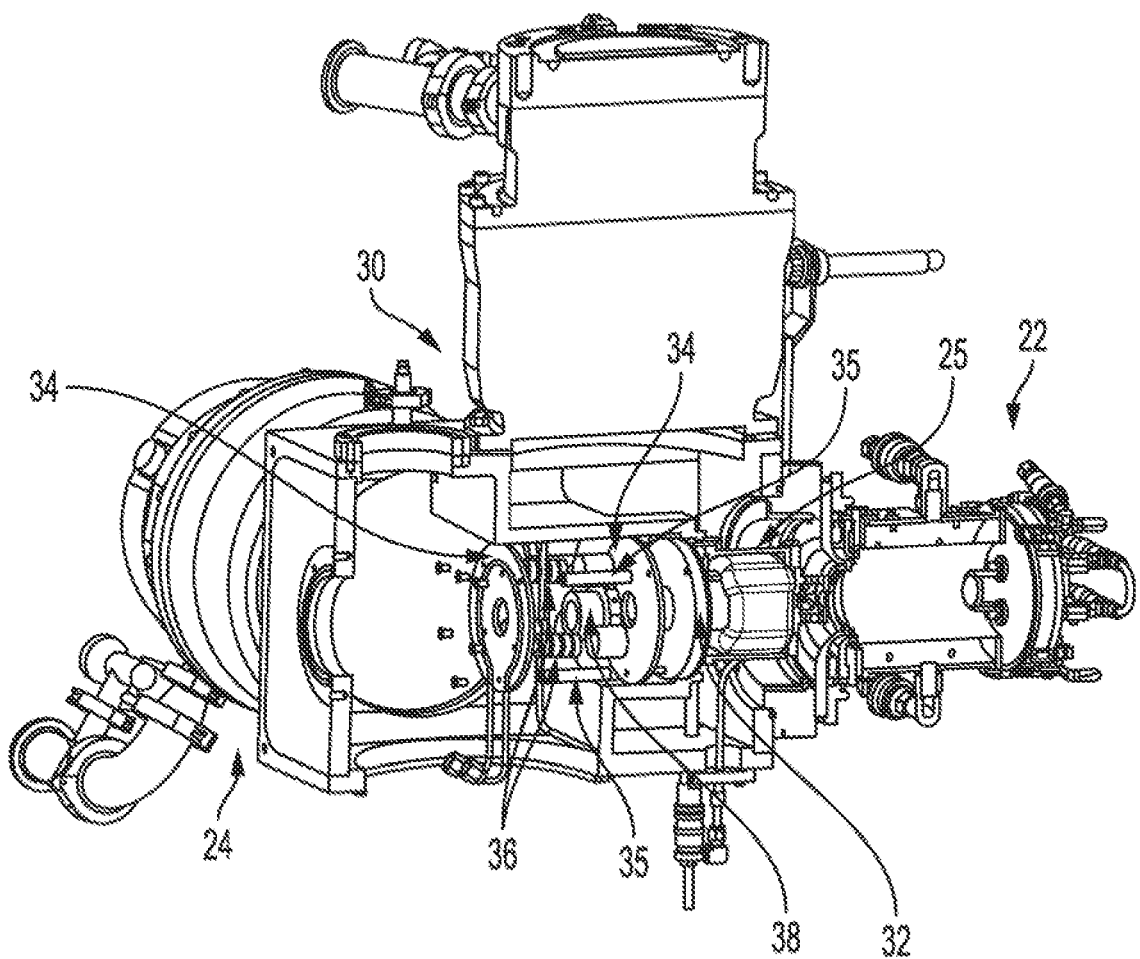
FIG. 4 is an exploded perspective view depicting an example embodiment of the einzel lens shown in FIG. 3.

Turning to FIG. 3, the ion source vacuum box 24 of the ion beam injector 20 includes an einzel lens 30 positioned therein. As shown in detail in FIG. 4, the einzel lens 30, which is mounted downstream of a ground lens 25 of the ion source 22 within the vacuum box 24, includes a mounting plate 32, two grounded electrodes 34 mounted to the mounting plate 32 and coupled to one of another in spaced relation with mounting rods 35, and a powered (biased) electrode 38 positioned between the two grounded electrodes 34. The electrodes 34 and 38 are made in the form of cylindrical apertures and assembled to have an axial axis coinciding with the beam path. The powered electrode 38 is supported by insulators/isolators 36 extending between the grounded electrodes or apertures 34.

The standoff isolators 36 may have a geometric design configured to inhibit development of electron avalanches and to suppress streamer formation and propagation which is typically ending up in a flashover formation. The geometric design of standoff isolators 36 may partially screen an external electric field on the insulator surface which drives the electron avalanche and effectively increases the path length. In addition, the materials of insulators/isolators 36 tend to diminish sputtering effects, loss of negative ions on surfaces, volume contamination, and formation of a conductive coating on the insulator/isolator surfaces leading to a decrease of electrical strength.

Functionally, action of the einzel lens 30 on the beam of charged particles advancing from the ion source 22 is akin to the action of optical focusing lens on a beam of light. Namely, the einzel lens 30 is focusing the incoming parallel beam into a spot at the focal plane. However, here the electric fields formed between the pairs of the powered electrode 38 and the two grounded electrodes 34 determine the focusing strength of the einzel lens (focal length distance).

By mounting the einzel lens 30 downstream of the ion source ground lens 25, it diminishes beam free space transportation where the beam is subjected to divergence due to intrinsic space charge.

The dimensions of the axisymmetric design of the einzel lens 30 can be optimized to avoid direct interaction of extracted ions with exposed surfaces of the einzel lens 30.

In operation, negative polarity biasing of the einzel lens 30 results in higher focusing power over the positive bias polarity. Also in operation, the method of power delivery to the einzel lens 30 can provide for gradual voltage growth instead of instantaneous voltage application, which reduces growth rates of electric field (dE/dt) at micro-protrusions existing on surfaces of the biased einzel lens 30 electrode responsible for plasma formation via, for example, an explosive emission mechanism. Impeding such plasma formation improves electrical strength.

Negative bias potential for an einzel lens in high background gas pressure is usually not possible due to electrical breakdowns. The configuration of the example embodiments of the einzel lens provided herein, enables the application of negative bias voltages sufficiently high for the 100% current utilization without electrical breakdowns.

Figure 5A:
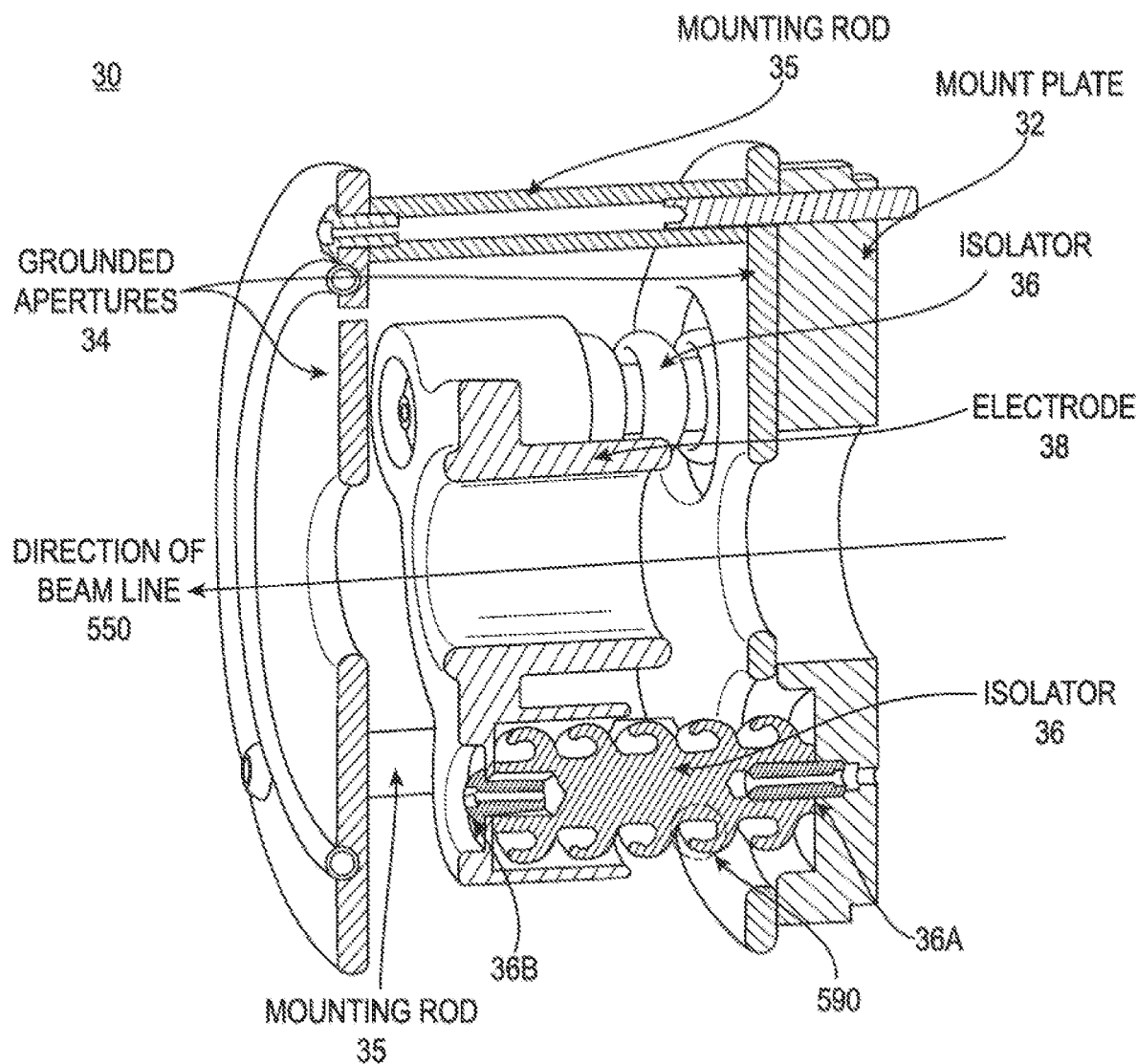
FIG. 5A illustrates an example einzel lens with electrode standoff isolation, for use with embodiments of the present disclosure.

FIG. 5A illustrates an einzel lens 30 with examples of electrode standoff isolation. In FIG. 5A, the example einzel lens 30 includes two grounded electrodes 34 mounted in the mounting or mount plate 32 and coupled to one another in spaced relation with mounting rods 35, and a powered (biased) electrode 38 positioned between the two grounded electrodes 34. The electrodes 34 and 38 are made in the form of cylindrical apertures and assembled to have an axial axis coinciding with the beam path. The powered electrode 38 is supported by standoff isolators 36 extending between the grounded electrodes or apertures 34. The standoff isolators 36 for mounting the powered electrode 38 preferably provide electrical insulation sufficient to stand off any potential difference between the surfaces of the mount plate 32 and the electrode 38.

While FIG. 5A depicts the standoff isolators 36 being additionally protected within a hollowed space of the high voltage electrode 38, such protection is an example embodiment.

Figure 5B:
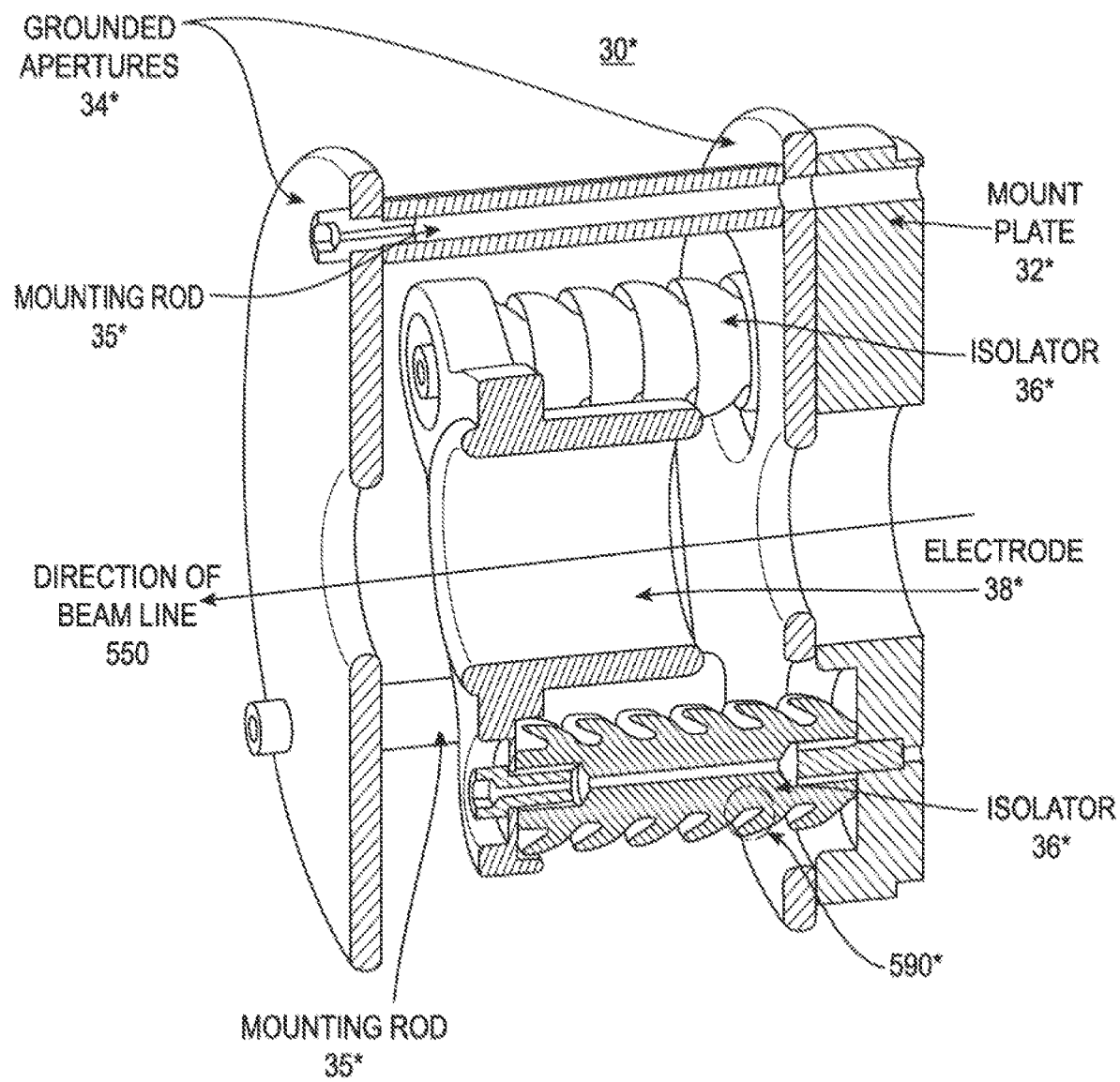
FIG. 5B illustrates an example einzel lens with electrode standoff isolation, for use with embodiments of the present disclosure.

FIG. 5B illustrates another embodiment of an einzel lens 30* with examples of electrode standoff isolation. FIG. 5B illustrates an einzel lens 30* with two grounded electrodes 34* mounted to the mounting or mount plate 32* and coupled to one another in spaced relation with mounting rods 35*, and a powered (biased) electrode 38* positioned between the two grounded electrodes 34*. The electrodes 34* and 38* are made in the form of cylindrical apertures and assembled to have an axial axis coinciding with the beam path. The powered electrode 38* is supported by standoff isolators 36* extending between the grounded electrodes or apertures 34*. The standoff isolators 36* for mounting the powered electrode 38* preferably provide electrical insulation sufficient to stand off any potential difference between the surfaces of the mount plate 32* and the electrode 38*. In FIG. 5B, the standoff isolator 36* is not positioned or protected within a hollowed space the high voltage electrode 38*.

While the standoff isolators 36, 36* preferably provide electrical insulation sufficient to stand off any potential difference between the surfaces of the mount plate 32, 32* and the powered electrode 38, 38*, the standoff isolators 36, 36* provide a surface upon which contaminants may form a conductive layer, leading to elimination of the insulation provided by the standoff isolators 36 and defeating their purpose. Moreover, the standoff isolators 36, 36* preferably provide sufficient electrical insulation while avoiding impeding passage of an ion beam through the einzel lens 30, 30*. Accordingly, embodiments of standoff isolators herein can have a beneficial geometry for maximizing surface area of the standoff isolator to provide sufficient insulative properties while allowing passage of an ion beam through the einzel lens as well as avoiding deposition of contaminants on the surface area.

A geometrical design for example standoff isolators described herein can have one or more overhanging ribs or sections, such that the overhanging ribs or sections provide a surface upon which deposition from a gaseous phase is especially difficult. The one or more overhanging ribs or sections may be shaped as cups, cupped sections, or flaps that are deflected toward a distal end 36B of the standoff isolator 36. As shown in FIG. 5A, the overhanging ribs are situated such that a direction 550 of the beam line passing through the einzel lens travels from a proximal end 36A toward a distal end 36B of the standoff isolator 36 and the direction of travel 550 of the beam is along, rather than against, the curvature of the overhanging ribs. In some embodiments, a direction of the beam line passing through the einzel lens may travel from a distal end 36B toward a proximal end 36A of the standoff isolator 36 such that the direction of travel of the beam is against the curvature of the overhanging ribs.

The one or more sections may be cupped such that the overhanging ribs or flaps create one or more shaded or shadow regions 590, 590* such that the shadow region is a shaded a surface area protected against deposition. A shadow region may have a varying range of shade associated therewith in order to be afforded some level of protection against deposition. The shadow regions may include a ring shape around part or all of a circumference of the standoff isolator.

Selection of a number of overhanging ribs or sections for inclusion in a design of a standoff isolator is dependent upon an applied voltage for which the standoff isolator is to provide electrical insulation (e.g., a total potential drop of 20 kV may lead to a plurality of structures each capable of withstanding a potential drop of 10 kV). While embodiments depicted herein include varying numbers of sections, the number of sections is selected in accordance with a preferred voltage drop the standoff isolator is to withstand. For example, a standoff isolator may preferably withstand a given total potential drop, and therefore the given total potential drop may be distributed across the plurality of sections of the standoff isolator. Accordingly, each section of the standoff isolator may be designed to withstand at least a subset of the total potential drop.

Each of a plurality of overhanging ribs or sections of an example standoff isolator may be separated from another overhanging rib or section by a predefined distance. Each predefined distance between subsequent sets of overhanging ribs or sections may be identical, or may vary depending upon the applied voltage and application within which the standoff isolator is situated.

A curvature of an overhanging rib of an example standoff isolator may be designed according to properties associated with an ion beam intended to pass by the standoff isolator. In ion sources, gaseous phase filament particles can tend to travel in a somewhat straight line originating from the upstream ion source through the einzel lens, and therefore past a proximal end of the standoff isolator and then past the distal end of the standoff isolator. In addition, gaseous phase filament particles may collide with residual gas and be partially ionized within the region of the ion beam transport thus facilitating formation of deposit on surfaces facing the ion beam yet may not reach surfaces that are not directly facing the ion beam. By introducing the overhanging rib and controlling its curvature, standoff isolators of the present disclosure introduce surface areas that are less subjected to deposit formation. Surface areas less subjected to deposit formation enable the standoff isolators to function as insulators for extended periods of time and for several uses. Moreover, selection of standoff material with specific properties (e.g., lower secondary particle emission coefficient) reduces further the amount of deposited conductive layer.

A geometry of an overhanging rib may be based on an angle of the most-difficult-to-reach surface of the standoff isolator relative to the beamline. The geometry may be based upon maximizing such an angle so that filament particles might have to change direction several times to reach the most-difficult-to-reach surface. A geometry of overhanging ribs may also take into account ease of manufacture, gap width between and number of ribs. For example, too small of a gap width between ribs may allow for undesirable arcing between one rib and the next.

Standoff isolators for use with embodiments of the present disclosure may include one or more materials having properties sufficient to withstand an applied voltage (e.g., to withstand a potential difference across two surfaces between which the standoff isolator is positioned). Such materials may be selected based upon resistive, conductive, and/or temperature coefficient properties of the materials. For example, materials used to manufacture the standoff isolators may include a grit blasted 3D printed opaque white SLA plastic that behaves similarly to polycarbonate (e.g., PerFORM). Example materials may be ceramic-filled and have elevated heat resistance.

FIGS. 6A, 6B, 6C, and 6D illustrate an example embodiment of an electrode standoff isolator, for use with embodiments of the present disclosure. An example electrode standoff isolator 600 includes a plurality of sections 601A, 601B, 601C, 601D, and 601E positioned between a proximal end 602A and a distal end 602B of the standoff isolator 600. The standoff isolator 600 is configured for an ion beam passing the standoff isolator to have a direction of travel 610 from the proximal end 602A to the distal end 602B.

Each of the plurality of sections 601A, 601B, 601C, 601D, and 601E is arranged in proximity to an adjacent section, such as in an at least partially overlapping manner. Each section may be a discrete physical entity and attached during manufacturing to an adjacent section at an adjoining point 603A, 603B, 603C, 603D, respectively. That is, sections 601A and 601B are attached at adjoining point 603A, sections 601B and 601C are attached at adjoining point 603B, sections 601C and 601D are attached at adjoining point 603C, and sections 601D and 601E are attached at adjoining point 603D. Alternatively, the standoff isolator 600 may be a monolithic or unitary structure where each section is formed from the same single body.

A diameter of each section of the plurality of sections 601A, 601B, 601C, 601D, and 601E may be larger than a diameter of each adjoining point of the adjoining points 603A, 603B, 603C, 603D. A length 604 of the example electrode standoff isolator 600 may be determined based upon dimensions of the einzel lens (or other application) within which the standoff isolator 600 may be situated.

Figure 6A:
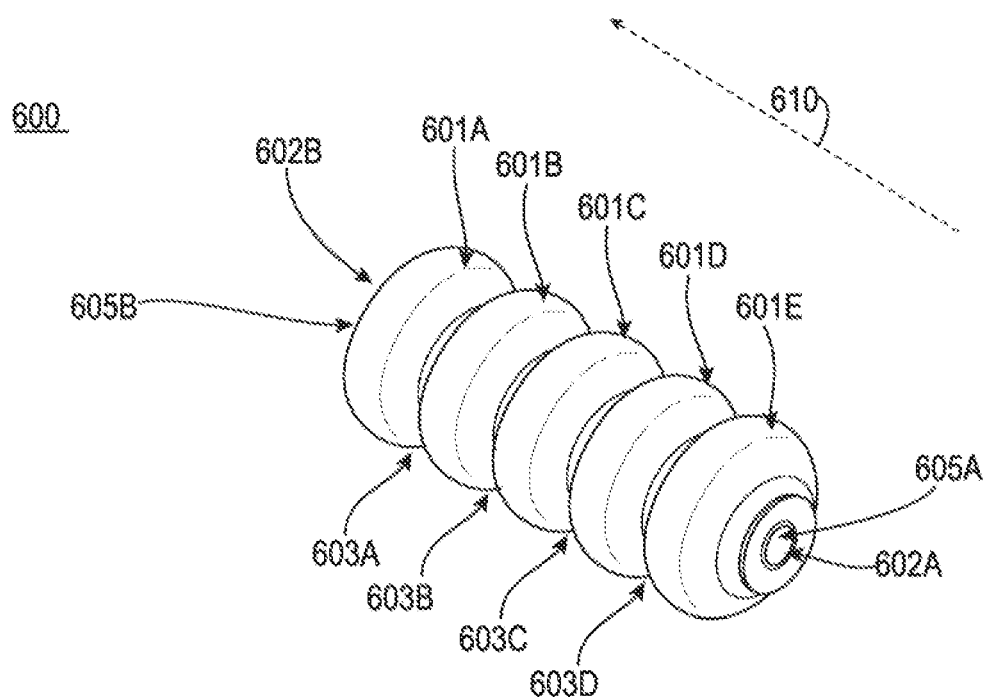
FIGS. 6A, 6B, 6C, and 6D illustrate an example embodiment of an electrode standoff isolator standoff, for use with embodiments of the present disclosure.
Figure 6B:
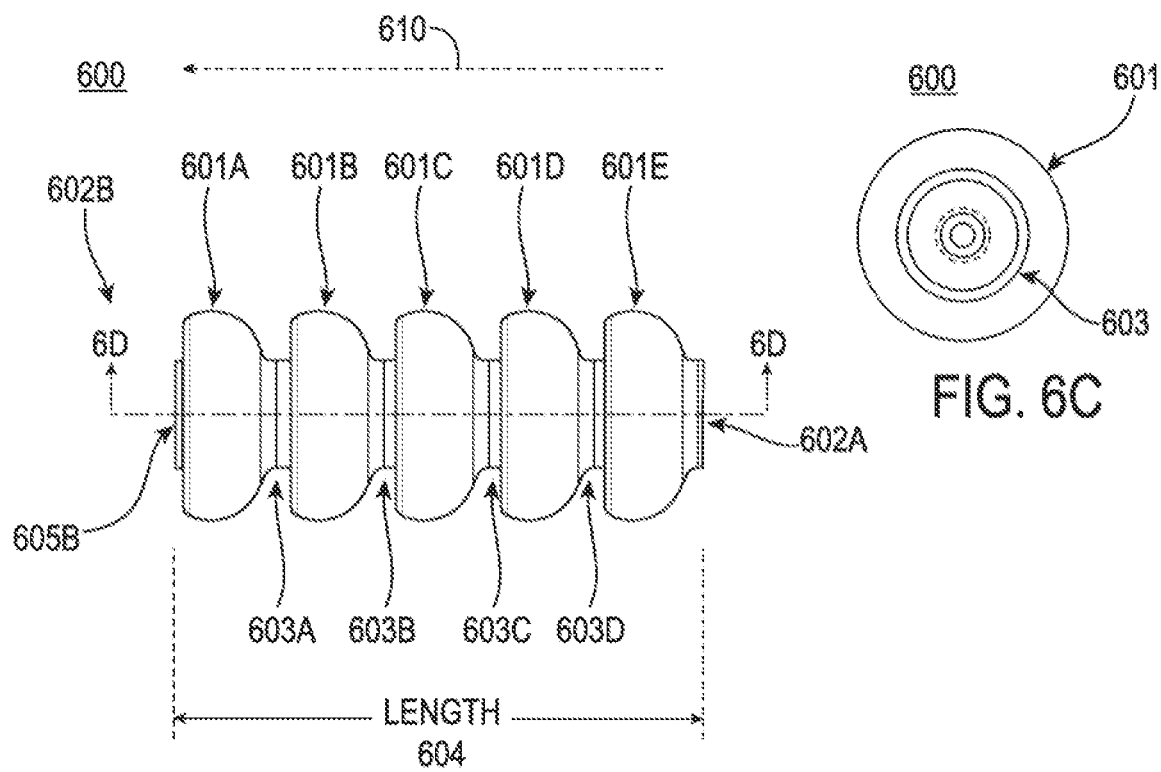
Figure 6C:
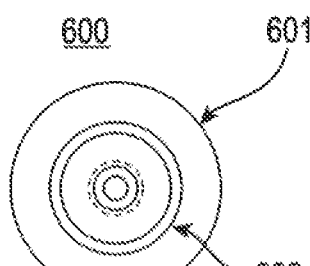
Figure 6D:
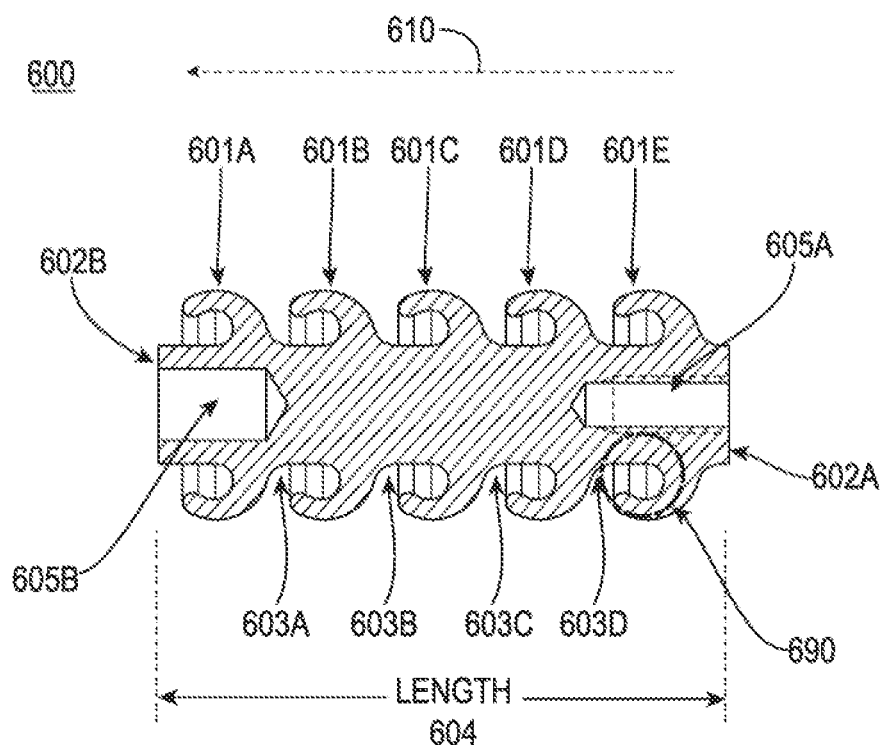
Figure 7A:
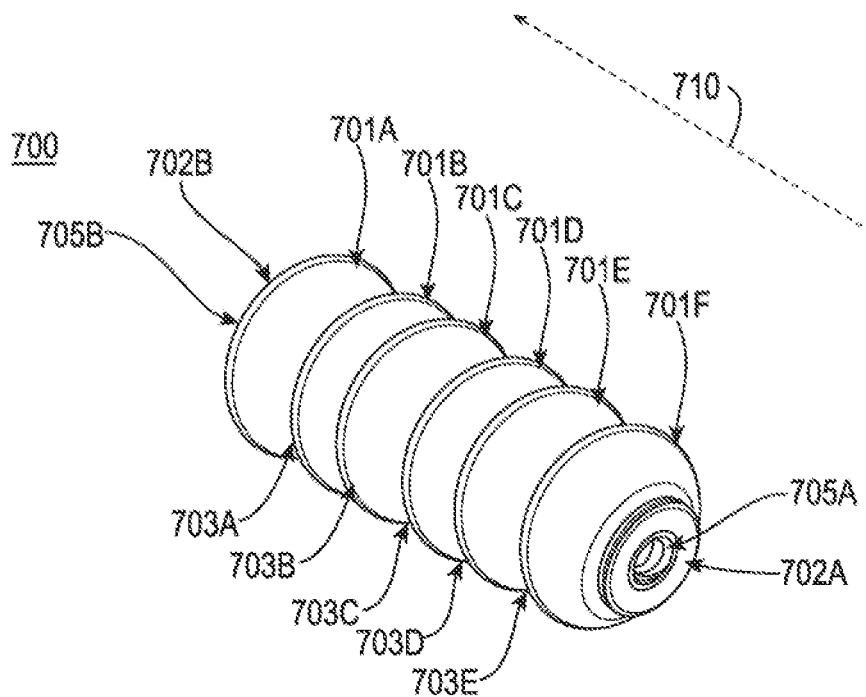

As shown in FIG. 6D, each section of the plurality of sections 601A, 601B, 601C, 601D, and 601E has an overhanging rib that discontinues into a body of the electrode standoff isolator such that an opening does not remain under the overhanging rib. Such design eliminates the possibility of formation of an alternative conductive path. Moreover, that each section of the plurality of sections has a complete band around the body of the isolator further eliminates the possibility of formation of an alternative conductive path.

Also shown in FIG. 6D, each overhanging rib is curved such that it deflects toward the distal end 602B of the standoff isolator 600. The one or more sections may be cupped such that the overhanging ribs or flaps create one or more shaded or shadow regions 690 and/or 603A-603D such that the shadow region is a shaded a surface area protected against deposition.

An example electrode standoff isolator 600 further includes connectors (or threads) 605A, 605B for attaching to, in an einzel lens application, a powered electrode (e.g., electrode 38, 38\* in FIGS. 5A-5B) and a mount plate (e.g., mount plate 32, 32\* in FIGS. 5A-5B).

FIGS. 7A, 7B, 7C, and 7D illustrate an alternative example embodiment of an electrode standoff isolator, for use with embodiments of the present disclosure. An example electrode standoff isolator 700 includes a plurality of sections 701A, 701B, 701C, 701D, 701E, and 701F positioned between a proximal end 702A and a distal end 702B of the standoff isolator 700. The standoff isolator 700 is configured for an ion beam passing the standoff isolator to have a direction of travel 710 from the proximal end 702A to the distal end 702B.

Each of the plurality of sections 701A, 701B, 701C, 701D, 701E, and 701F is arranged in proximity to an adjacent section, such as in an at least partially overlapping manner. Each section may be a discrete physical entity and attached during manufacturing to an adjacent section at an adjoining point 703A, 703B, 703C, 703D, 703E respectively. That is, sections 701A and 701B are attached at adjoining point 703A, sections 701B and 701C are attached at adjoining point 703B, sections 701C and 701D are attached at adjoining point 703C, sections 701D and 701E are attached at adjoining point 703D, and sections 701E and 701F are attached at adjoining point 703E. Alternatively, the standoff isolator 700 may be a monolithic or unitary structure where each section is formed form the same single body.

Each of the plurality of sections 701A, 701B, 701C, 701D, 701E, and 701F includes an overhanging rib that slightly differs in curvature from those depicted in the example embodiment of FIGS. 6A-6D. Simplicity in manufacturing allowing utilization of various processing methods may lead to selection of different curvatures or geometries herein.

A diameter of each section of the plurality of sections 701A, 701B, 701C, 701D, 701E, and 701F may be larger than a diameter of each adjoining point of the adjoining points 703A, 703B, 703C, 703D, 703E. A length 704 of the example electrode standoff isolator 700 may be determined based upon dimensions of the einzel lens (or other application) within which the standoff isolator 700 may be situated.

As shown in FIG. 7D, each section of the plurality of sections 701A, 701B, 701C, 701D, 701E, and 701F has an overhanging rib that discontinues into a body of the electrode standoff isolator such that an opening does not remain under the overhanging rib. Such design eliminates the possibility of formation of an alternative conductive path. Moreover, that each section of the plurality of sections includes a complete band around the body of the isolator further eliminates the possibility of formation of an alternative conductive path.

Also shown in FIG. 7D, each overhanging rib is curved such that it deflects toward the distal end 702B of the standoff isolator 700. The one or more sections may be cupped such that the overhanging ribs or flaps create one or more shaded or shadow regions 790 and/or 703A-703E such that the shadow region is a shaded a surface area protected against deposition.

An example electrode standoff isolator 700 further includes connectors (or threads) 705A, 705B for attaching to, in an einzel lens application, a powered electrode (e.g., electrode 38, 38\* in FIGS. 5A-5B) and a mount plate (e.g., mount plate 32, 32\* in FIGS. 5A-5B).

FIGS. 8A, 8B, 8C, and 8D illustrate yet another alternative embodiment of an electrode standoff isolator, for use with embodiments of the present disclosure. An example electrode standoff isolator 800 includes a plurality of sections 801A, 801B positioned between a proximal end 802A and a distal end 802B of the standoff isolator 800. The standoff isolator 800 is configured for an ion beam passing the standoff isolator to have a direction of travel 810 from the proximal end 802A to the distal end 802B.

Sections 801A and 801B are arranged in proximity to one another, such as in an at least partially overlapping manner.

Each section may be a discrete physical entity and attached during manufacturing at an adjoining point 803. Alternatively, the standoff isolator 600 may be a monolithic or unitary structure where each section is formed form the same single body.

Each of the plurality of sections 801A and 801B has an overhanging rib that slightly differs in curvature from those depicted in the example embodiments of FIGS. 6A-6D and 7A-7D. In the example embodiment shown in FIG. 8D, a given section is uniform in curvature and has a horizontal exterior surface between rounded edges. The embodiments depicted in FIG. 8D may provide for an increase in path complexity for conductive particles such that a conductive path is unlikely to form on an outer edge of the inner ring of the isolator.

A diameter of each section of the plurality of sections 801A, 801B may be larger than a diameter of the adjoining point 803. A length 804 of the example electrode standoff isolator 800 may be determined based upon dimensions of the einzel lens (or other application) within which the standoff isolator 800 may be situated.

The sections 801A, 801B may be designed to create a shadow region at adjoining point 803 such that the shadow region is a shaded a surface area protected against deposition.

Figure 8D:
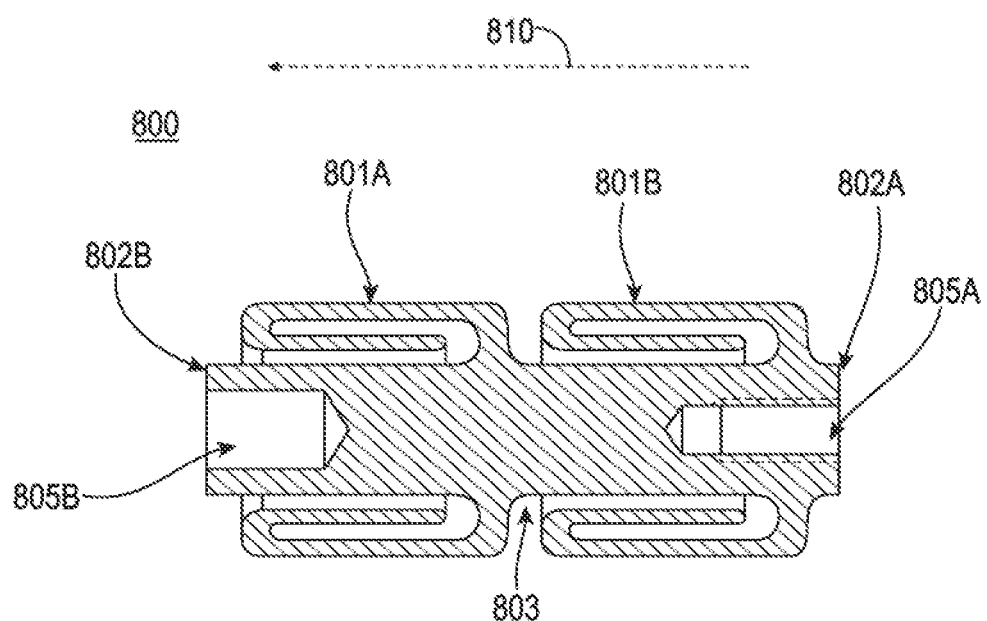

As shown in FIG. 8D, each section of the plurality of sections 801A, 801B has an overhanging rib that discontinues into a body of the electrode standoff isolator such that an opening does not remain under the overhanging rib. Such design eliminates the possibility of formation of an alternative conductive path. Moreover, that each section of the plurality of sections has a complete band around the body of the isolator further eliminates the possibility of formation of an alternative conductive path.

An example electrode standoff isolator 800 further includes connectors (or threads) 805A, 805B for attaching to, in an einzel lens application, a powered electrode (e.g., electrode 38, 38* in FIGS. 5A-5B) and a mount plate (e.g., mount plate 32, 32* in FIGS. 5A-5B.

FIGS. 9A, 9B, 9C, and 9D illustrate yet another alternative embodiment of an electrode standoff isolator, for use with embodiments of the present disclosure. An example electrode standoff isolator 900 includes a plurality of sections 901A, 901B, 901C, and 901D positioned between a proximal end 902A and a distal end 902B of the standoff isolator 900. The standoff isolator 900 is configured for an ion beam passing the standoff isolator to have a direction of travel 910 from the proximal end 902A to the distal end 902B. In other embodiments, the direction of travel may be from the distal end 902B toward the proximal end 902A.

Each of the plurality of sections 901A, 901B, 901C, 901D is arranged in proximity to an adjacent section, such as in an at least partially overlapping manner. Each section may be a discrete physical entity and attached during manufacturing to an adjacent section at an adjoining point 903A, 903B, 903C respectively. That is, sections 901A and 901B are attached at adjoining point 903A, sections 901B and 901C are attached at adjoining point 903B, sections 901C and 901D are attached at adjoining point 903C. Alternatively, the standoff isolator 900 may be a monolithic or unitary structure where each section is formed form the same single body.

Each of the plurality of sections 901A, 901B, 901C, and 901D has an overhanging rib that slightly differs in curvature from those depicted in the example embodiment of FIGS. 6A-6D, 7A-7D, 8A-8D.

A diameter of each section of the plurality of sections 901A, 901B, 901C, 901D may be larger than a diameter of each adjoining point of the adjoining points 903A, 903B, 903C. A length 904 of the example electrode standoff isolator 900 may be determined based upon dimensions of the einzel lens (or other application) within which the standoff isolator 900 may be situated.

Figure 9D:
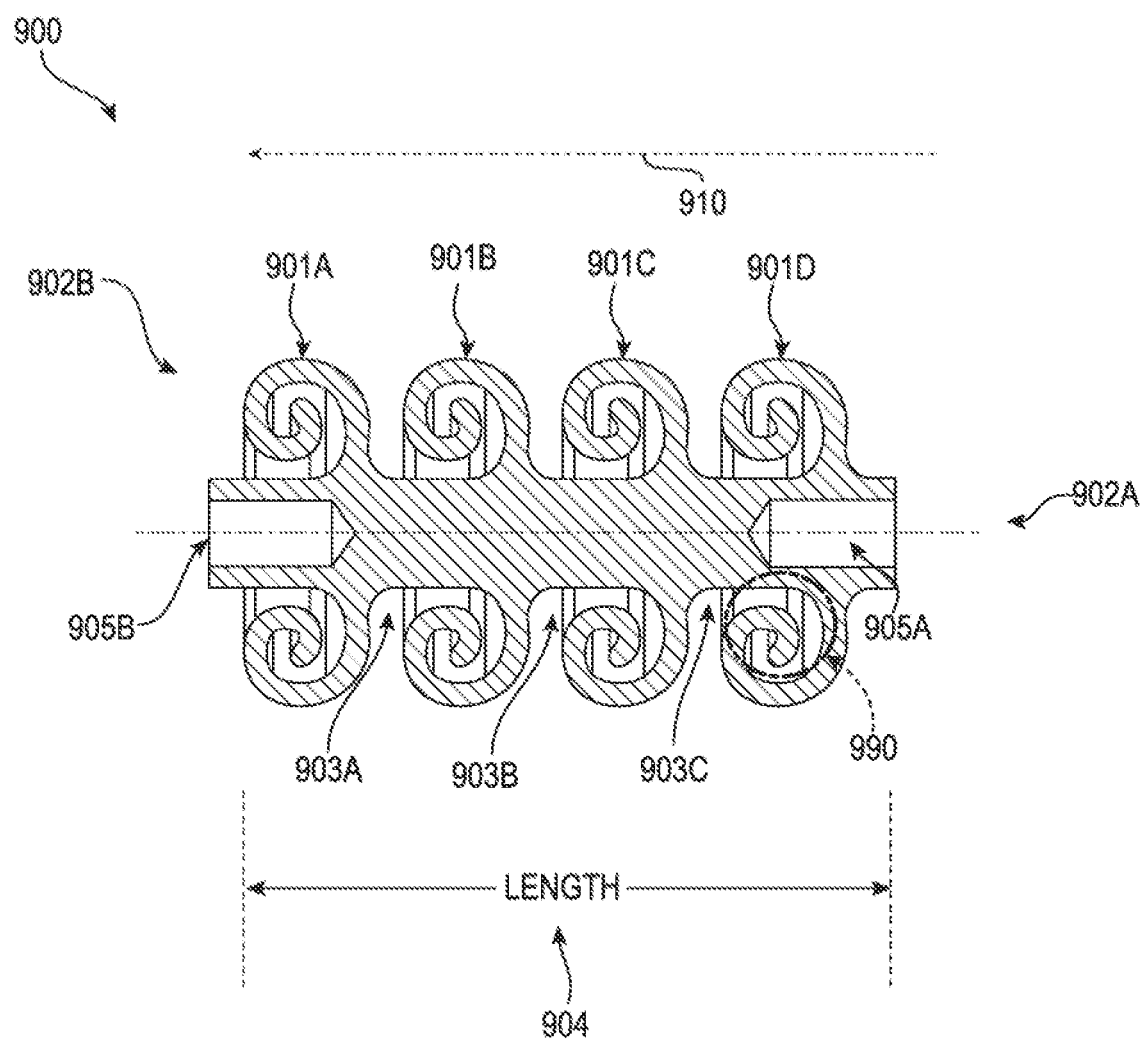

As shown in FIG. 9D, each section of the plurality of sections 901A, 901B, 901C, 901D includes an overhanging rib that discontinues into a body of the electrode standoff isolator such that an opening does not remain under the overhanging rib. Such design eliminates the possibility of formation of an alternative conductive path. Moreover, that each section of the plurality of sections includes a complete band around the body of the isolator further eliminates the possibility of formation of an alternative conductive path.

Also shown in FIG. 9D, each overhanging rib is curved such that it deflects toward the distal end 902B of the standoff isolator 900. The one or more sections may be cupped such that the overhanging ribs or flaps create one or more shaded or shadow regions 990 and/or 903A-903C such that the shadow region is a shaded a surface area protected against deposition.

An example electrode standoff isolator 900 further includes connectors (or threads) 905A, 905B for attaching to, in an einzel lens application, a powered electrode (e.g., electrode 38, 38* in FIGS. 5A-5B) and a mount plate (e.g., mount plate 32, 32* in FIGS. 5A-5B).

Figure 10:
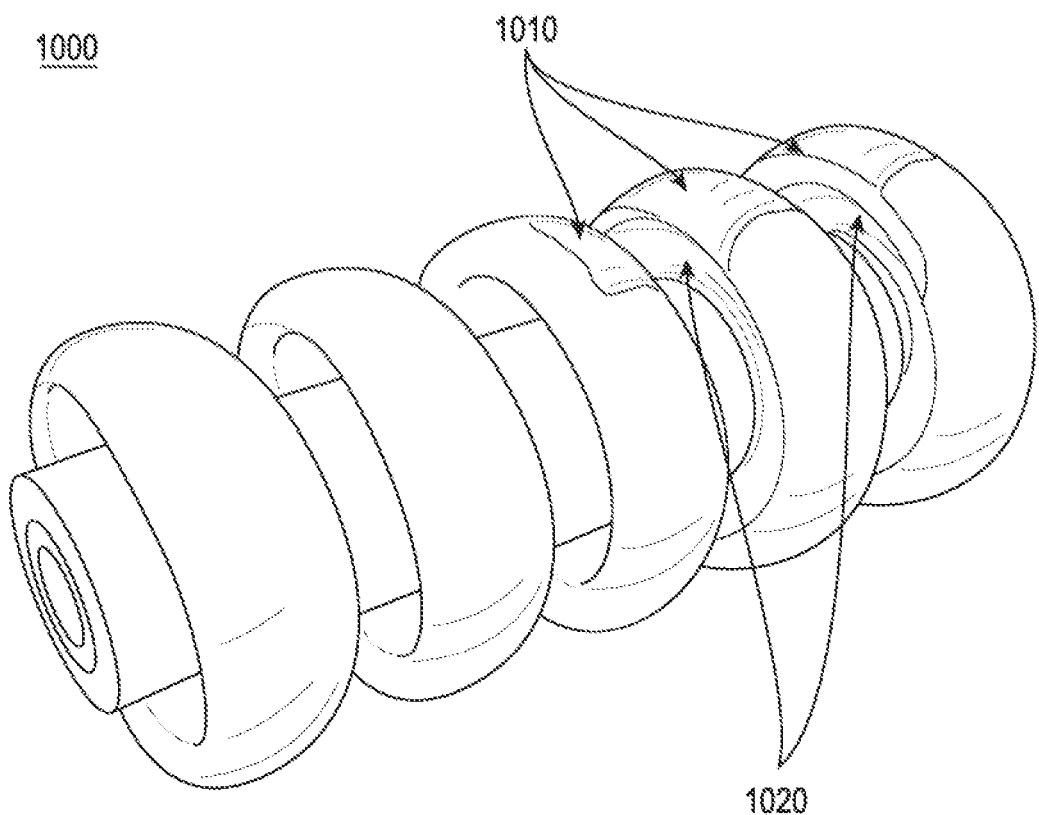
FIG. 10 illustrates reduced contamination of an example electrode standoff isolator, according to embodiments described herein.

FIG. 10 illustrates reduced contamination of an example electrode standoff isolator, according to embodiments described herein. Shown in FIG. 10, an example electrode standoff isolator 1000 configured according to embodiments described herein, includes visible deposits of contaminants 1010 on its exterior surface after having been used in an einzel lens within an ion beam system for BNCT. In contrast to exterior surfaces 1010, shadowed areas 1020 of standoff 1000 show no or minimal deposition of contaminants, which results in the standoff isolator continuing to provide electrical insulation without impeding passage of the ion beam.

While embodiments depicted herein may have a round and/or symmetrical geometry for each section or overhanging rib area of the standoff isolator, non-rounded edges may be employed in a standoff isolator design without departing from the scope of the present disclosure. Moreover, asymmetrical geometries for each section or overhanging rib area of the standoff isolator may be employed as well. While embodiments depicted herein include a plurality of seemingly identical sections or overhanging rib areas, a standoff isolator having a plurality of sections or overhanging rib areas, where one or more of the sections or overhanging rib areas differs in design, shape, dimension, or the like form the others, may be employed without departing from the scope of the present disclosure.

Yet further alternative embodiments may employ a plurality of curves along the surface of the standoff isolator such that the exterior is spiral in design.

The standoff isolators described herein may be manufactured in any suitable manner, including 3-D printing. The geometric design of the present standoff isolators is optimized for simplified single-piece fabrication using methods of additive manufacturing using composite material.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many embodiments, an electrode standoff isolator comprises a plurality of adjacent insulative segments positioned between a proximal end and a distal end of the electrode standoff isolator. In these embodiments, a geometry of the plurality of adjacent insulative segments is configured to guard a surface area of the electrode standoff isolator against deposition of a conductive layer of gaseous phase materials from a filament of an ion source.

In many of these embodiments, dimensions of adjacent insulative segments of the plurality of adjacent insulative segments configure the electrode standoff isolator to withstand a potential difference across two surfaces between which the electrode standoff isolator is positioned while an ion beam passes along its proximal end toward its distal end.

In many of these embodiments, an insulative segment comprises an overhanging rib connected at its underside to a body of the electrode standoff isolator.

In many of these embodiments, the electrode standoff isolator further includes one or more threads for attaching to one or more surfaces.

In many of these embodiments, the potential difference is 20 kV.

In many of these embodiments, each adjacent insulative segment of the plurality of adjacent insulative segments includes substantially equivalent dimensions.

In many of these embodiments, one or more adjacent insulative segment of the plurality of adjacent insulative segments includes differing dimensions from one or more other adjacent insulative segments of the plurality of adjacent insulative segments.

In many of these embodiments, each adjacent insulative segment comprises material suitable to withstand a subset of the potential difference.

In many of these embodiments, the electrode standoff isolator has a length associated with dimensions of an einzel lens within which the electrode standoff isolator is situated.

In many of these embodiments, each adjacent insulative segment is separated from its immediate neighboring adjacent insulative segment by a distance. In many of these embodiments, a first distance between a first pair of adjacent insulative segments is different from a second distance between a second pair of adjacent insulative segments.

In many of these embodiments, the electrode standoff isolator includes a maximum surface area for withstanding the potential difference while allowing passage of an ion beam through an einzel lens and avoiding deposition of contaminants on the surface area.

In many of these embodiments, each adjacent insulative segment includes a curvature. In many of these embodiments, the ion beam passes along the curvature. In many of these embodiments, the ion beam passes against the curvature.

In many of these embodiments, the geometry of a given adjacent insulative segment provides a shadow region on one or more of a first surface area of an immediate adjacent insulative segment or a second surface area of the electrode standoff isolator. In many of these embodiments, the shadow region is guarded against deposition of a conductive layer of gaseous phase materials from a filament of an ion source.

In many of these embodiments, the electrode standoff isolator includes 3D printed opaque plastic.

In many of these embodiments, the electrode standoff isolator includes a ceramic filling.

In many of these embodiments, the electrode standoff isolator includes a standalone monolithic body.

In many embodiments, a method of reducing deposition of contaminants on a surface area of an electrode standoff isolator includes positioning a plurality of adjacent insulative segments positioned between a proximal end and a distal end of the electrode standoff isolator, and configuring a geometry of the plurality of adjacent insulative segments to guard the surface area of the electrode standoff isolator against deposition of a conductive layer of gaseous phase materials from a filament of an ion source.

In many of these embodiments, the method includes configuring dimensions of adjacent insulative segments of the plurality of adjacent insulative segments to withstand a potential difference across two surfaces between which the electrode standoff isolator is positioned while an ion beam passes along its proximal end toward its distal end.

In many of these embodiments, the insulative segment includes an overhanging rib connected at its underside to a body of the electrode standoff isolator.

In many of these embodiments, the method includes creating one or more threads within the electrode standoff isolator for attaching to one or more surfaces.

In many of these embodiments, the potential difference is 20 kV.

In many of these embodiments, the method includes configuring each adjacent insulative segment of the plurality of adjacent insulative segments to have substantially equivalent dimensions.

In many of these embodiments, the method includes configuring one or more adjacent insulative segment of the plurality of adjacent insulative segments to have differing dimensions from one or more other adjacent insulative segments of the plurality of adjacent insulative segments.

In many of these embodiments, the method includes generating each adjacent insulative segment using material suitable to withstand a subset of the potential difference.

In many of these embodiments, the method includes configuring a length of the electrode standoff isolator according to einzel lens dimensions of an einzel lens within which the electrode standoff isolator is situated.

In many of these embodiments, the method includes separating each adjacent insulative segment from its immediate neighboring adjacent insulative segment by a distance. In many of these embodiments, the method includes separating a first pair of adjacent insulative segments by a first distance between and separating a second pair of adjacent insulative segments by a second distance.

In many of these embodiments, the electrode standoff isolator comprises a maximum surface area for withstanding the potential difference while allowing passage of an ion beam through an einzel lens and avoiding deposition of contaminants on the surface area.

In many of these embodiments, the method includes configuring each adjacent insulative segment with a curvature. In many of these embodiments, the method includes propagating the ion beam along the curvature. In many of these embodiments, the method includes propagating the ion beam against the curvature.

In many of these embodiments, the method includes configuring the geometry of a given adjacent insulative segment to provide a shadow region on one or more of a first surface area of an immediate adjacent insulative segment or a second surface area of the electrode standoff isolator, wherein the shadow region is guarded against deposition of a conductive layer of gaseous phase materials from a filament of an ion source.

In many embodiments, an einzel lens includes two grounded electrodes coupled to one another in spaced relation and a biased electrode positioned therebetween, wherein the biased electrode is supported by electrode standoff isolators according to any of the aforementioned embodiments.

In many of these embodiments, the einzel lens includes one or more cupped sections within which electrode standoff isolators are situated.

In many embodiments, a low energy beamline (LEBL) includes an ion source and an einzel lens according to any of the aforementioned embodiments mounted adjacent and downstream of a ground lens of the ion source.

In many embodiments, a neutron beam system includes a high voltage (HV) accelerator, a high-energy beamline (HEBL) coupled to an output of the high voltage (HV) accelerator, and a low-energy beamline (LEBL) coupled to an inlet of the high voltage (HV) accelerator. In many of these embodiments, the low-energy beamline (LEBL) includes an einzel lens according to any of the aforementioned embodiments.

In many embodiments, an insulative structure includes a plurality of adjacent insulative segments positioned between a proximal end and a distal end of the structure. In many of these embodiments, a geometry of the plurality of adjacent insulative segments is configured to guard a surface area of the electrode standoff isolator against deposition of a conductive layer of gaseous phase materials.

In many of these embodiments, dimensions of adjacent insulative segments of the plurality of adjacent insulative segments configure the structure to withstand a potential difference across two surfaces between which the structure is configured to be positioned when in use within a beam system.

In many of these embodiments, the potential difference is 20 kV.

In many of these embodiments, a first insulative segment of the plurality of insulative segments comprises an overhanging rib having an underside adjoining a body of the structure. In many of these embodiments, the insulative structure includes one or more threads for attaching to one or more surfaces.

In many of these embodiments, each adjacent insulative segment of the plurality of adjacent insulative segments is configured with substantially equivalent dimensions.

In many of these embodiments, one or more adjacent insulative segments of the plurality of adjacent insulative segments has differing dimensions from one or more other adjacent insulative segments of the plurality of adjacent insulative segments.

In many of these embodiments, each adjacent insulative segment has a curved surface.

In many of these embodiments, a geometry of a given adjacent insulative segment provides a shadow region.

In many of these embodiments, a geometry of a given adjacent insulative segment provides a shadow region on one or more of a first surface area of an immediate adjacent insulative segment or a second surface area of the insulative structure, wherein the shadow region is guarded against deposition of a conductive layer of gaseous phase materials.

In many of these embodiments, the insulative structure is configured according to any of the aforementioned embodiments.

In many of these embodiments, the insulative structure according to any of the aforementioned embodiments is configured for use in a beam system according to any of the aforementioned embodiments.

In many of these embodiments, the insulative structure according to any of the aforementioned embodiments is configured for use in an electrostatic lens, quadrupole, or magnetic focusing device of a beam system.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An electrode standoff isolator, comprising:
a plurality of adjacent insulative segments positioned between a proximal end and a distal end of the electrode standoff isolator, wherein each adjacent insulative segment of the plurality of insulative segments comprises a curved surface that deflects toward the distal end of the electrode standoff isolator,
wherein a geometry of the plurality of adjacent insulative segments is configured to guard a surface area of the electrode standoff isolator against deposition of a conductive layer of gaseous phase materials from a filament of an ion source.

2. The electrode standoff isolator of claim 1, wherein dimensions of adjacent insulative segments of the plurality of adjacent insulative segments configure the electrode standoff isolator to withstand a potential difference across two surfaces between which the electrode standoff isolator is positioned while an ion beam passes along its proximal end toward its distal end.

3. The electrode standoff isolator of claim 2, wherein the potential difference is 20 kV.

4. The electrode standoff isolator of claim 2, wherein each adjacent insulative segment comprises material suitable to withstand a subset of the potential difference.

5. The electrode standoff isolator of claim 2, wherein the electrode standoff isolator comprises a maximum surface area configured to:

withstand the potential difference while allowing passage of an ion beam through an einzel lens within which the electrode standoff isolator is situated and avoid deposition of contaminants on the surface area.

6. The electrode standoff isolator of claim 1, wherein an insulative segment comprises an overhanging rib connected at its underside to a body of the electrode standoff isolator.

7. The electrode standoff isolator of claim 6, wherein each overhanging rib is separated from its immediate neighboring overhanging rib by a distance.

8. The electrode standoff isolator of claim 7, wherein a first distance between a first pair of overhanging ribs is different from a second distance between a second pair of overhanging ribs.

9. The electrode standoff isolator of claim 1, further comprising one or more threads for attaching to one or more surfaces.

10. The electrode standoff isolator of claim 1, wherein each adjacent insulative segment of the plurality of adjacent insulative segments comprises substantially equivalent dimensions.

11. The electrode standoff isolator of claim 1, wherein one or more adjacent insulative segment of the plurality of adjacent insulative segments comprises differing dimensions from one or more other adjacent insulative segments of the plurality of adjacent insulative segments.

12. The electrode standoff isolator of claim 1, having a length associated with dimensions of an einzel lens within which the electrode standoff isolator is situated.

13. The electrode standoff isolator of claim 1, configured to be oriented such that the ion beam passes in a direction along a curvature of the curved surface.

14. The electrode standoff isolator of claim 1, configured to be oriented such that the ion beam passes in a direction against a curvature of the curved surface.

15. The electrode standoff isolator of claim 1, wherein the geometry of a given adjacent insulative segment provides a shadow region on one or more of a first surface area of an immediate adjacent insulative segment or a second surface area of the electrode standoff isolator, wherein the shadow region is guarded against deposition of a conductive layer of gaseous phase materials from a filament of an ion source.

16. The electrode standoff isolator of claim 1, further comprising 3D printed opaque plastic.

17. The electrode standoff isolator of claim 1, further comprising a ceramic filling.

18. The electrode standoff isolator of claim 1, further comprising a standalone monolithic body.

19. A method of reducing deposition of contaminants on a surface area of an electrode standoff isolator, the method comprising:

positioning a plurality of adjacent insulative segments between a proximal end and a distal end of the electrode standoff isolator; and configuring a geometry of the plurality of adjacent insulative segments to guard the surface area of the electrode standoff isolator against deposition of a conductive layer of gaseous phase materials from a filament of an ion source, wherein each adjacent insulative segment of the plurality of insulative segments comprises a curved surface that deflects toward the distal end of the electrode standoff isolator.

\* \* \* \* \*